US012797427B2

(12) United States Patent
Leskauskaitė et al.

(10) Patent No.: US 12,797,427 B2
(45) Date of Patent: Nov. 17, 2026

(54) CO-ENCAPSULATED PROBIOTICS AND PREBIOTIC DIETARY FIBERS IN FOOD GRADE MULTIPHASE GEL SYSTEM AND USE THEREOF IN FATTY PRODUCTS

(71) Applicant: Kaunas University of Technology, Kaunas (LT)

(72) Inventors: Daiva Leskauskaitė, Kaunas (LT); Aušra Šipailienė, Kaunas (LT); Viktorija Eisinaitė, Kaunas (LT); Michail Syrpas, Kaunas (LT)

(73) Assignee: Kaunas University of Technology, Kaunas (LT)

( * ) Notice: Subject to any disclaimer, the term of this patent is extended or adjusted under 35 U.S.C. 154(b) by 495 days.

(21) Appl. No.: 18/366,962

(22) Filed: Aug. 8, 2023

(65) Prior Publication Data

US 2025/0049875 A1 Feb. 13, 2025

(51) Int. Cl.

| | |
|---|---|
| ***A61K 36/45*** | (2006.01) |
| ***A23D 7/005*** | (2006.01) |
| ***A23D 7/04*** | (2006.01) |
| ***A23L 19/00*** | (2016.01) |
| ***A23L 33/135*** | (2016.01) |
| ***A23L 33/22*** | (2016.01) |
| ***A61K 9/06*** | (2006.01) |

(Continued)

(52) U.S. Cl.

CPC ............ *A61K 36/45* (2013.01); *A23D 7/0056* (2013.01); *A23D 7/04* (2013.01); *A23L 19/09* (2016.08); *A23L 33/135* (2016.08); *A23L 33/22* (2016.08); *A61K 9/06* (2013.01); *A61K 31/733* (2013.01); *A61K 35/747* (2013.01); *A61K 36/185* (2013.01); *A61K 47/42* (2013.01); *A61K 47/44* (2013.01); *A23V 2400/173* (2023.08); *A61K 2035/115* (2013.01)

(58) Field of Classification Search

CPC .... A61K 36/45; A61K 35/747; A61K 36/185; A61K 47/44; A23L 19/09; A23L 33/22; A23L 33/135; A23D 7/0056; A23D 7/0053

USPC ................................ 426/573, 585, 583, 602

See application file for complete search history.

(56) References Cited

U.S. PATENT DOCUMENTS

2009/0208606 A1* 8/2009 Hakansson ............ A23L 7/104 426/18
2024/0407409 A1* 12/2024 Leskauskaite .......... A23L 33/22

FOREIGN PATENT DOCUMENTS

CN 112970929 A 5/2021
CN 115316648 A 7/2022

(Continued)

OTHER PUBLICATIONS

Novel Formulation of Bigel-Based Vegetable Oil Spreads enriched in Lingonberry Pomace, Foods, Jul. 25, 2022, (Baltuonyte) (Year: 2022).*

(Continued)

*Primary Examiner* — Jennifer McNeil
(74) *Attorney, Agent, or Firm* — Koivula & Somersalo LLC

(57) ABSTRACT

A food grade double gel system or bigel is disclosed. The bigel comprises an oleogel phase and a hydrogel phase. The Oleogel phase comprises vegetable oil and a gelator, and the hydrogel phase comprises collagen. The bigel further comprises co-encapsulated probiotics and prebiotic soluble dietary fibers. Disclosed are also food products comprising the bigel as well as method for preparing the bigel.

8 Claims, 9 Drawing Sheets

(51) Int. Cl.

| | |
|---|---|
| ***A61K 31/733*** | (2006.01) |
| ***A61K 35/747*** | (2015.01) |
| ***A61K 36/185*** | (2006.01) |
| ***A61K 47/42*** | (2017.01) |
| ***A61K 47/44*** | (2017.01) |
| *A61K 35/00* | (2006.01) |

(56) References Cited

FOREIGN PATENT DOCUMENTS

| | | | |
|---|---|---|---|
| CN | 115399376 | A | 11/2022 |
| GB | 2445539 | A | 7/2008 |

OTHER PUBLICATIONS

The Effect of Encapsulating a Prebiotic-Based Biopolymer Delivery System for Enhanced Probiotic Survival, Polymers, Mar. 31, 2023 (Kistaubayeva) (Year: 2023).*

Bigel formulations based on sesame oleogel with probiotics alginate hydrogel: A novel structure for nutritious spreadable butter, International Journal of Biological Macromolecules (May 9, 2023) (Hashim) and (Year: 2023).*

FAO/WHO. (2002). Guidelines for the Evaluation of Probiotics in Food. Report of a Joint FAO/WHO Working Group on Drafting Guidelines for the Evaluation of Probiotics in Food. Apr. 30 and May 1, 2002, 11 pages.

Razavi, S., S. Janfaza, N. Tasnim, D. L. Gibson & M. Hoorfar. (2021). Microencapsulating polymers for probiotics delivery systems: Preparation, characterization, and applications. Food Hydrocolloids, 120, Article 106882; 9 pages.

Frakolaki, G., V. Giannou, D. Kekos, & C. Tzia. (2021). A review of the microencapsulation techniques for the incorporation of probiotic bacteria in functional foods. Critical Reviews in Food Science and Nutrition, 61(9), Article 1515-1536.

Shori, A. B. (2015). The potential applications of probiotics on dairy and non-dairy foods focusing on viability during storage. Biocatalysis and Agricultural Biotechnology, 4(4), Article 423-431.

De Vos, P., Faas, M. M., Spasojevic, M., & Sikkema, J. (2010). Encapsulation for preservation of functionality and targeted delivery of bioactive food components. International Dairy Journal, 20(4), Article 292-302.

Van Baarlen, P. F. J., Troost, S., Van Hemert, C., Van Der Meer, W. M., de Vos, P. J., de Groot, G. J. E. J., Hooiveld, R. J. M., Brummer, R. J., & Kleerebezem. M. (2009). Differential NF-B pathways induction by Lactobacillus plantarum in the duodenum of healthy humans correlating with immune tolerance. Proceedings of the National Academy of Sciences of the United States of America (PNAS), 106(7), Article 2371-2376.

Martins, A., Cerqueira, M., Fasolin, L., Cunha, R., & Vicente, A. (2016). Beeswax organogels: Influence of gelator concentration and oil type in the gelation process. Food Research International 84, Article 170-179.

Singh, V. K., Qureshi, D., Nayak, S. K., & Pal, K. (2018). Bigels. In Polymeric gels (pp. 265-282), Book Chapter, Woodhead Publishing.

Angelerou, M. G. F., Markus, R., Paraskevopoulou, V., Foralosso, R., Clarke, P., Alvarez, C., Chenlo, M., Angel, M., Johnson, L., Rutland, C., Allen, S., Brasnett, C., Seddon, A., Zelzer, M., & Marlow, M. (2020). Mechanistic investigations into the encapsulation and re-lease of small molecules and proteins from a supramolecular nucleoside gel in vitro and in vivo. Journal of Controlled Release, 317, Article 118-129.

Chen, H., Dai, H., Zhu, H., Ma, L., Fu, Y., Feng, X., & Sun, Y., Zhang, Y. (2021). Construction of dual-com-partmental microdroplet via shrimp ferritin nanocages stabilized Pickering emulsions for co-encapsulation of hydrophobic/hydrophilic bioactive compounds. Food Hydrocolloids, 126, Article 107443. 10 pages.

Okonkwo, C. E., Ofoedu, C. E., Hussain, S. Z., Adeyanju, A. A., Naseer, B., Inyinbor, A. A., Olaniran, A. F., & Kamal-Eldin, A. (2022). Application of biogels for bioactives delivery: Recent developments and future research insights. Applied Food Research, 2, Article 100238. 23 pages.

Zheng, H., Mao, L., Cui, M., Liu, J., & Gao, Y. (2020). Development of food-grade bigels based on beta-carrageenan hydrogel and monoglyceride oleogels as carriers for • -carotene: Roles of oleogel fraction. Food Hydrocolloids, 105, Article 105855. 8 pages.

Liu, K., Huang, R. L., Zha, X. Q., Li, Q. M., Pan, L. H., & Luo, J. P. (2020). Encapsulation and sustained release of curcumin by a composite hydrogel of lotus root amylopectin and chitosan. Carbohydrate Polymers, 232, Article 115810. 8 pages.

Martinez, R. M., Magalhães, W. V., da Silva Sufi, B., Padovani, G., Nazato, L. I. S., Velasco, M. V. R., Lannes, S. C. D. S., & Baby, A. R. (2021). Vitamin E-loaded bigels and emulsions: Physicochemical characterization and potential biological application. Colloids and Surfaces B: Biointerfaces, 201, Article 111651. 10 pages.

Mousavi, S. N., Hosseini, E., Dorraji, M. S. S., Mohammadi, S. S., Pourmansouri, Z., Ra-soulifard, M. H., Doosti, M., & Chiti, H. (2021). Synthesis of a green bigel using cottonseed oil/cannabis oil/alginate/ferula gum for quercetin release: Synergistic effects for treating infertility in rats. International Journal of Biological Macromolecules, 177, Article 157-165.

Zhu, Q., Gao, J., Han, L., Han, K., Wei, W., Wu, T., Li, J., & Zhang, M. (2021). Development and char-acterization of novel bigels based on monoglyceride-beeswax oleogel and high acyl gellan gum hydrogel for lycopene delivery. Food Chemistry, 365, Article 130419. 9 pages.

Behera, B., Sagiri, S., Singh, V. K., Pal, K., & Anis, A. (2014). Mechanical properties and delivery of drug/probiotics from starch and non-starch based novel bigels: A comparative study. Starch—Stärke, 66(9-10), Article 865-879.

Zhuang, X., Clark, S., & Acevedo, N. (2021). Bigels—oleocolloid matrices—as probiotic protective systems in yogurt. Journal of Food Science, 86(11), Article 4892-4900.

Bollom, M. A., Clark, S., & Acevedo, N. C. (2021). Edible lecithin, stearic acid, and whey protein bigels enhance survival of probiotics during in vitro digestion. Food Bioscience, 39, Article 100813. 7 pages.

Gibson, G. R., Hutkins, R., Sanders, M. E., Prescott, S. L., Reimer, R. A., Salminen, S. J., Scott, K., Stanton, C., Swanson, K. S., Cani, P. D., Verbeke, K., & Reid, G. (2017). Expert consensus document: The International Scientific Association for Probiotics and Prebiotics (ISAPP) consensus statement on the definition and scope of prebiotics. Nature reviews Gastroenterology & hepatology, 14(8), Article 491-502.

Lordan, C., Thapa, D., Ross, R. P., & Cotter, P. D. (2020). Potential for enriching next-generation health-promoting gut bacteria through prebiotics and other dietary components. Gut Microbes, 11(1), Article 1-20.

Augustin, L. S. A., Aas, A. M., Astrup, A., Atkinson, F. S., Baer-Sinnott, S., Barclay, A. W., Brand-Miller, J. C., Brighenti, F., Bullo, M., Buyken, A. E., Ceriello, A., Ellis, P. R., Ha, M. A., Henry, J. C., Kendall, C. W. C., La Vecchia, C., Liu, S., Livesey, G., Poli, A., Salas-Salvadó, J., Riccardi, G., Riserus, U., Rizkalla, S. W., Sievenpiper, J. L., Trichopoulou, A., Usic, K., Wolever, T. M. S., Willett, W. C., & Jenkins, D. J. A. (2020). Dietary fibre consensus from the international carbohydrate quality consortium (ICQC). Nutrients, 12, Article 2553. 11 pages.

Espitia, P. J. P., Batista, R. A., Azeredo, H. M. C., & Otoni, C. G. (2016). Probiotics and their potential applications in active edible films and coatings. Food Research International, 90, Article 42-52.

Sathyabama, S., Ranjith kumar, M., Bruntha devi, P., Vijayabharathi, R., & Brindha priyadharisini, V. (2014). Co-encapsulation of probiotics with prebiotics on alginate matrix and its effect on viability in simulated gastric environment. LWT—Food Science and Technology, 57(1), Article 419-425.

Zaeim, D., Jamab, M. S., Ghorani, B., Kadkhodaee, R., Liu, W., & Tromp, R. H. (2020). Microencapsulation of probiotics in multi-polysaccharide microcapsules by electro-hydrodynamic atomization and incorporation into ice-cream formulation. Food Structure, 25, Article 100147. 20 pages.

Poletto, G., Raddatz, G. C., Cichoski, A. J., Zepka, L. Q., Lopes, E. J., Barin, J. S., Wagner, R., & de Menezes, C. R. (2019). Study of

(56) References Cited

OTHER PUBLICATIONS viability and storage stability of Lactobacillus acidophillus when encapsulated with the prebiotics rice bran, inulin and Hi-maize. Food Hydrocolloids, 95, Article 238-244.

Qin, X. S., Luo, Z. G., & Li, X. L. (2020). An enhanced pH-sensitive carrier based on alginate-Ca-EDTA in a set-type W1/O/W2 double emulsion model stabilized with WPI-EGCG covalent conjugates for probiotics colon-targeted release. Food Hydrocolloids, 113, Article 106460. 10 pages.

Kumherová, M., Veselá, K., Jokešová, K., Klojdová, I., & Horáčková, Š. (2020). Influence of co-encapsulation of *Bifidobacterium animalis* subsp. *lactis* Bb12 with inulin and ascorbic acid on its viability. Czech Journal of Food Science, 38(1), Article 57-62.

Huebner, J., Wehling, R. L. & Hutkins, R. W. (2007). Functional activity of commercial prebiotics. International Dairy Journal, 17, Article 770-775.

* cited by examiner

Figure 2 a, b, c

Figure 4 a, b a)
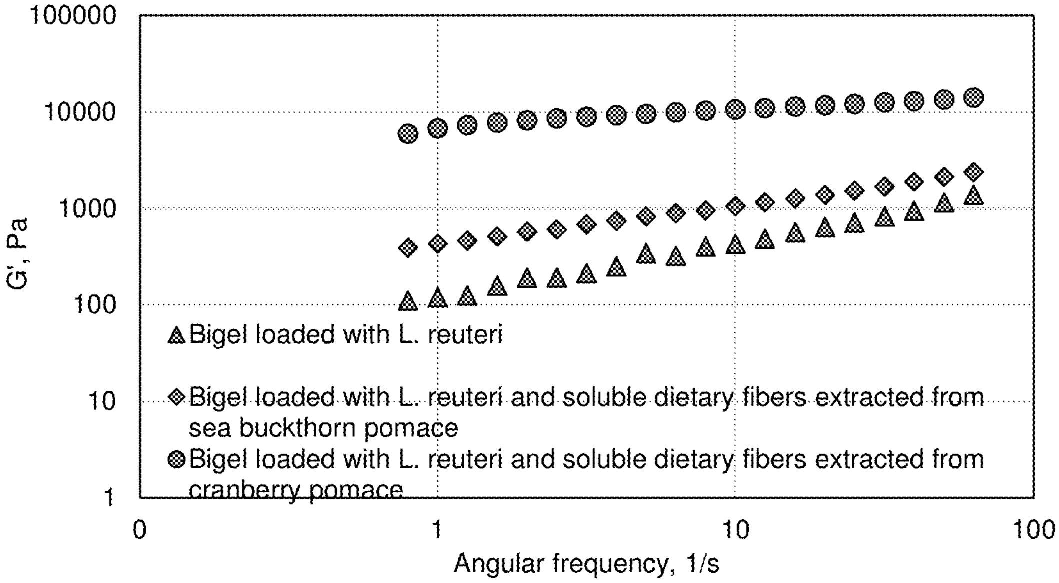
b)
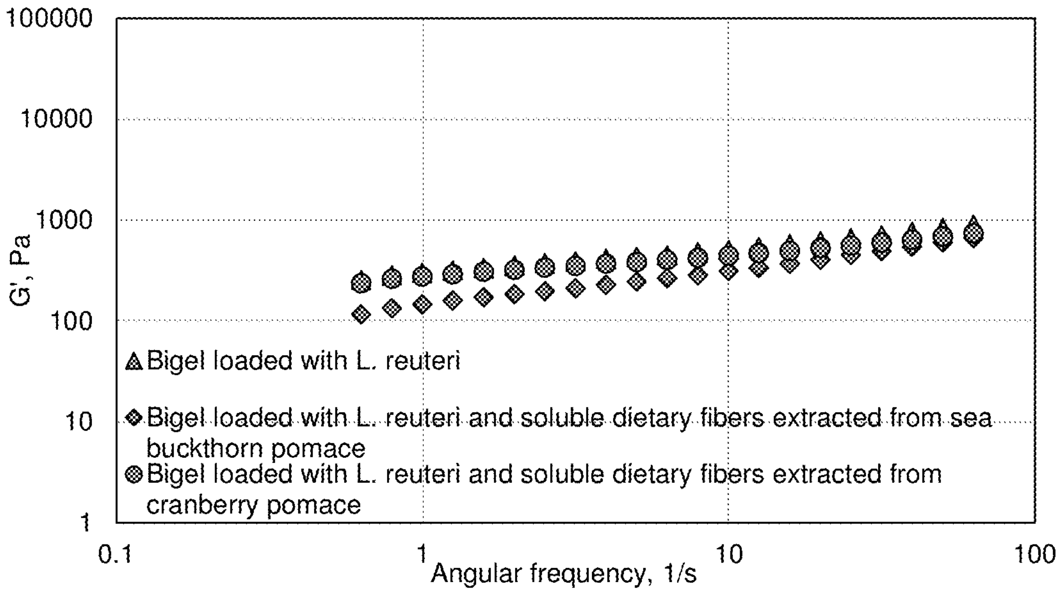
Figure 7a,b

CO-ENCAPSULATED PROBIOTICS AND PREBIOTIC DIETARY FIBERS IN FOOD GRADE MULTIPHASE GEL SYSTEM AND USE THEREOF IN FATTY PRODUCTS

FIELD OF INVENTION

The invention relates to the field of food technology. More precisely, it is a double-gel system comprising an oleogel around a hydrogel, in which probiotic cells and prebiotic dietary fibers are embedded, protecting probiotics from adverse environmental conditions, delivering viable probiotic cultures to the intestine, and exhibiting good functional properties.

BACKGROUND ART

Probiotic bacteria are major components of the human colon microbiota that have a symbiotic relationship with their host. According to the FAO/WHO, probiotic foods contain more than $10^6$ CFU/g of probiotic bacteria to achieve sufficient health benefits for the host ([1] FAO/WHO, 2002; [2] Razavi et al., 2021). Despite the fact that probiotic microorganisms have been successfully incorporated into a variety of food products, they can face a wide range of harsh conditions through the food manufacturing process, transportation, and storage, as well as, during the passage through the gastrointestinal tract ([3] Frakolaki et al., 2021; [4] Shori, 2015). Therefore, it is very important to have sufficiently viable microorganisms after the consumption of probiotic food in order to achieve the expected beneficial effect to host health.

In this respect, encapsulation of probiotics has been recognized as a successful way to preserve the cells under various environments ([5] de Vos et al., [6] 2010; van Baarlen et al., 2009). Extensive research has been carried out on the encapsulation of probiotics to maintain viability and targeted intestinal delivery, but less attention has been paid to the fact that these systems should also be suitable for food. Food products differ in their pH, ionic strength, water activity, and composition of nutrients. All these factors can increase or decrease the viability of probiotics in a product. In this context, the most significant attributes of the probiotic encapsulation system should be considered if these systems protect probiotic cells in food.

In recent years, two-phase gelation technology has shown significant progress in both fundamental research and practical application for the encapsulation of bioactive materials ([7] Martins et al., 2016). This delivery system is made by combining two immiscible gels at a high shear rate, which afterward exists as a uniform dispersion hydrogel-in-oleogel called bigel ([8] Singh, Qureshi, Nayak & Pal, 2018). Various technologies are used to produce two-phase gelled structures, such as surface coating with surfactants, 3D-printing, microwave hydro diffusion and gravity technology, electric field extrusion, cold gelation, double emulsion template, wax gelator, etc. Mechanical, structural, thermal, physical, and rheological properties of bigels are of prime importance for their successful utilization in food applications. Considering the use of bigels in food systems, it is very important that their components do not need additional processing or purification before use, they are tasteless and easy to swallow ([9] Angelerou et al., 2020; Chen et al., 2021). The final properties of the bigel system are highly dependent on the structural distribution of each phase within the bigels and care must be taken when incorporating a bigel into food to avoid changes in texture.

As delivery systems of food bioactive substances, bigels have advantages over other carriers due to their high nutritional value, excellent functional properties, biocompatibility, biodegradability, and low toxicity. The review of Cinton et al (2022) showed that bigels provide biocompatible, biodegradable, renewable, easy-to-obtain, inexpensive, non-toxic, and sustainable materials for food bioactive delivery. For instance, Zheng et al. (2020) showed good light and thermal stabilities of 8-carotene incorporated into bigel, Liu et al (2021) revealed better curcumin storage stability after encapsulation into bigel structure. Bigels with quercetin and tocopherol were developed by Mousavi et al (2021) and Martinez et al (2021). It is very important that the data presented in some studies prove that bigels can also be used for the controlled release of food bioactive ingredients, such as curcumin, lycopene, etc. ([16] Zhu et al., 2021, Zheng et. al., 2020).

Regardless of the listed advantages, two-phase gelation technology is not yet very common for the encapsulation of probiotics. Only a few studies focused on developing bigel that can serve as a vehicle for the delivery of probiotics. Behera et al. (2014) demonstrated that probiotic bacteria remained viable (above $10^8$ CFU/g) for 60 days after encapsulation of probiotic bacteria in a bigel prepared using a mixture of sorbitan monopalmitate (Span 40), sunflower oil and the mixture of polysaccharides. Zhuang et al. (2021) revealed that a gel-in-gel system (made using soy lecithin, stearic acid, and whey protein concentrate) was suitable for preserving the viability of *Bifidobacterium lactis* and *Lactobacillus acidophilus* cells when the encapsulated bacteria were used in yogurt production. In addition, this study showed that the viability of *Lactobacillus acidophilus* using the aforementioned encapsulation system during digestion was better than that of *Bifidobacterium lactis*. Bollom et al (2021) indicated that bigels with phospholipids may only be effective at increasing viability of *Bifidobacterium lactis* and *Lactobacillus acidophilus* bacteria inside products during stable conditions of shelf-life, not the conditions of an in vitro digestion system with acid, bile, and enzymes.

The few studies that have been carried out have shown that the use of bigels for the protection of probiotics from (1) adverse environmental conditions during food production and (2) release in the upper gastrointestinal tract with the aim to release them in the colonic environment where complex microbiota is residing have several limiting aspects:

1) Probiotics encapsulated in bigels are insufficiently protected from degradation during storage. According to available data probiotics in bigels remain viable for up to 60 days, and after adding them to food products, their viability does not change only for 3-6 weeks. Therefore, it is important to pay special attention to preserving the viability of encapsulated probiotics for a longer period of time-up to 10-12 months;
2) Probiotics can face difficulties in surviving through the bigel manufacturing process due to a wide range of harsh conditions (thermal treatment, high shear rate);
3) Delivering viable probiotic cultures to the gut has been a challenging problem. The effect of hydrogel-in-oleogel processing, shelf-life, and digestion on probiotic survival must be addressed during development of this encapsulation system.

The present invention solves the above-listed problems by co-encapsulating probiotics and prebiotics in bigel system, which enables to get high viability of probiotics during encapsulation, storage, addition into food products and protect them from the degradation in the upper gastrointestinal tract.

Several studies have observed that combining probiotic bacteria with prebiotic compounds, improves their viability during the food production and storage processes and even in in vitro digestion tests ([23] Espitia et al., 2016). In the study of Kumherova et al. (2020), encapsulated *Bifidobacterium animalis* subsp. *lactis* Bb12, together with the well-known prebiotic inulin and/or ascorbic acid by emulsifying in a milk protein matrix or by extrusion in an alginate matrix. Both encapsulation methods had a positive effect on the resistance of Bb12 cells under the conditions of the gastrointestinal model compared to non-encapsulated cells. Also, during storage for up to 6 weeks in sterile milk at +6±1 °C, the number of Bb12 bacteria encapsulated together with inulin remained almost unchanged as well. [25] D. Zaeim et al. (2020) demonstrated that encapsulation of *L. plantarum* ATCC 8014 and *B. animalis* subsp. *Lactis* in calcium-alginate/chitosan microcapsules together with inulin and resistant starch improved the viability of these bacteria. *Lactobacillus acidophilus* combined with prebiotics (rice bran, inulin or modified starch) in calcium alginate microgels was found to improve probiotic viability under different storage and gastrointestinal conditions ([26] Poletto et al., 2019). Encapsulation of *Lactobacillus plantarum* and prebiotics (fructooligosaccharides) in the internal aqueous phase of double emulsions protected the probiotics and increased their viability ([27] Quin et al., 2021). All these studies suggest that co-encapsulation of suitable combinations of prebiotics in the bigel system can be used to increase the viability of probiotics and improve their biological activity.

Over 20 years ago, a class of compounds, termed prebiotics, were recognized for their ability to stimulate the activity of beneficial intestinal bacteria and their growth as probiotic bacteria in the host ([20] Gibson et al., 2017). The most extensively documented dietary prebiotics are galactans, fructans, xylo-oligosaccharides, isomalto-oligosaccharides, lactulose ([20] Gibson et al., 2017). Some dietary fibers are also reported to act as prebiotics by being a substrate for the fermentation of potentially beneficial bacteria in the gastrointestinal tract, thus influencing the composition and metabolism of bacterial communities ([21] Lordan, Thapa, Ross, & Cotter, 2020). But not all dietary fiber corresponds to the concept of prebiotics. Currently, there is sufficient knowledge in the literature about the prebiotic action of water-soluble dietary fibers, such as oligosaccharides—fructans (fructooligosaccharides, oligofructose, and inulin) and galactans ([21] Lordan et al., 2020). S. Sathyabama et al. (2014) investigated renewable dietary fiber sources such as sugar beet and chicory, which are rich in potential prebiotics, oligosaccharides that can be co-encapsulated with the probiotic strains *Enterococcus fecium* and *Staphylococcus succinus*. This study showed that sugar beet prebiotics increase resistance to bile salts, while chicory prebiotics increase the intestinal environment. Furthermore, there is evidence that the interaction of dietary fiber with other components of the food matrix, especially phenolic compounds, modulates the gut microbiota more effectively than the consumption of purified commercial fibers ([22] Augustin et al., 2020). According to Kumherova et al. (2020), the combination of prebiotic inulin with antioxidant ascorbic acid encapsulated with probiotic bacteria better preserve sensitive bacteria during processing and storage.

Therefore, in our opinion food grade bigels used for the encapsulation of probiotics should contain water soluble dietary fibers, extracted from berry pomace, which are rich in fructans, galactans and phenolic compounds. Since there is currently no evidence of prebiotic activity of water-soluble dietary fibers extracted from berry pomace, it is necessary to find suitable combination of water soluble dietary fibers and probiotic bacteria for co-encapsulation in food-grade bigel system having the following characteristics: (1) it should maintain the stability of the probiotics in the food composition and in the gastrointestinal environment; (2) it should release the probiotics when they reach the colon so they can colonize the lower gastrointestinal tract.

According to the object of the invention, the closest patent document to the present invention is UK patent application GB2445539A of the priority date of Jul. 16, 2008, describing a method for producing a bigel that can be used to deliver a pharmaceutical or cosmetic composition. The method comprises steps: providing an oleogel comprising at least one oily agent gelled with at least one cellulose polymer; providing an aqueous gel comprising at least one component whose viscosity is pH dependent, such as a carbomer; mixing the oleogel and the aqueous gel together to form a bigel; and subsequently adjusting the viscosity of the bigel under high flow and low shear stirring to obtain a bigel of a desired viscosity.

The application CN115316648A discloses a double-gel composition and a preparation method thereof. In terms of weight percentage, the double-gel composition includes 0.12-0.25% of plant polyphenols, 32.5-63.7% of oil, and 0.75-0.75% of oil-phase gel 2.9%, 0.15-1.2% of water-phase gel agent, 0.2-0.61% of additives, and the balance is water, wherein the plant polyphenols include at least one of mangiferin, naringin and naringenin. In this disclosure, special types of plant polyphenols are embedded in the double-gel system, which can increase the loading capacity and stability of plant polyphenols in the double-gel system.

The Chinese patent application CN115399376A discloses a method of double-gel fat preparation method and 3D printing application. According to the method natural wax and small molecule emulsifier are dissolved in vegetable oil to obtain an oil gel solution and water-soluble polysaccharide is dissolved in water, to obtain hydrogel solution. Then the oil gel solution and the hydrogel solution are mixed and homogenized to obtain a double-gel emulsion, and then gelled to obtain a double-gel fat. Different types of double-gel fat substitutes have obvious applicability differences for 3D printing models, and can be customized for different appearance types of fats.

The Chinese patent application CN112970929A discloses a probiotic preparation based on W1/O/W2 type double emulsion structure. The preparation process comprises the following steps of: mixing a solution containing probiotic thalli or the probiotic thalli with a probiotic protective agent to serve as an internal water phase W1; dissolving an emulsifier in a lipid phase to form a lipid phase O, preliminarily mixing the lipid phase O with the internal water phase W1, and performing stirring and emulsification by a low-energy emulsification method or a high-energy emulsification method to obtain primary emulsion W1/O; and taking the solution of the emulsifier as an external water phase W2, adding W2 into the primary emulsion W1/O, and performing stirring and emulsification by the low-energy emulsification method or the high-energy emulsification method to obtain W1/O/W2 type double emulsion, namely the probiotic preparation. According to the probiotic preparation, the probiotic is embedded by adopting a double emulsion system, so that the probiotic keeps activity in the low-temperature storage and freeze-thaw processes, the influence of the external environment on the probiotic is reduced, and the storage and freeze-thaw stability of the probiotic in the shelf life of the product is improved.

However, these disclosures do not reveal the food-grade double-gel or bigel system as probiotics carriers protecting sensitive bacteria from degradation during processing and long term storage and delivering sufficient amounts of probiotics to the lower gastrointestinal tract to release them in the colonic environment where complex microbiota is residing.

The present invention emphasizes a lack of probiotics delivery systems that would:

- formulate double gel system consisting of oleogel around hydrogel in which embedded living cells and prebiotic dietary fibers to protect probiotics from adverse environmental conditions and to create a favorable microbiological environment for them;
- ensure the viability of probiotics during the technological process and long-term storage at +4 °C and −18 °C and when added to the food throughout its shelf-life;
- minimize the loss of probiotics throughout the gastrointestinal tract and thereby promote gut health benefits of food products made with them;
- provide excellent functional properties, and do not affect the appearance and structure of the food.

SUMMARY OF INVENTION

The present invention discloses a food-grade double-gel (bigel) composition comprising co-encapsulated probiotics and prebiotic dietary fibers in this food grade double-gel (bigel) system (system prepared according to a particular formula/composition) that provides a sufficient amount of viable probiotic cells protected from degradation during storage, minimizes their loss throughout the gastrointestinal tract, and thereby promotes gut health benefits of food products made with them. Further, the invention discloses a method for producing the aforementioned bigel composition, and also a food product comprising said bigel, and furthermore, use of the disclosed food-grade bigel composition in fatty food products.

The novelty of the present invention is the stable two-immiscible phase structure containing probiotic bacteria and prebiotic dietary fibers extracted from berry pomace, which allows to keep probiotics viable and control their release in the targeted place of the gastrointestinal tract. The concentration of proteins in the hydrogel phase, the distribution of fats in the oleogel phase, and the addition of probiotic bacteria and prebiotic dietary fibers extracted from berry pomace in the hydrogel phase provide such a synergistic effect that the phases thereof are balanced for high viability of probiotic cells during technological process, storage, application in food products and during the passage through the gastrointestinal tract after consumption. The prebiotic potential of water soluble dietary fibers extracted from berry pomace and their positive impact on the viability of *Lactobacillus reuteri* when co-loaded in the hydrogel phase of bigel system was investigated. The stability of the probiotics during 6 months storage at +4 °C and 12 months storage at −18 °C and when added to the food throughout its shelf-life was proven. The viability of probiotics under the upper gastrointestinal environment was investigated during the in vitro digestive degradation of the bigel containing probiorics. Simulated gastrointestinal activity is used in many food and nutrition sciences areas because human testing is often expensive, resource-intensive, and ethically controversial. In the development of probiotic delivery systems, in vitro digestive degradation is essential to show the delivery of viable probiotic cultures to the colonic environment where complex microbiota is residing in order to achieve the expected beneficial effect to host health.

The present invention solves problems and obtains the following effects:

- Despite encapsulation of probiotics has been recognized as a successful way to preserve the cells under various environments, there is a lack of food-compatible systems for the protection of probiotics. The major disadvantage of the known methods of adding probiotics to food is that they cause undesirable changes in food, which shorten the shelf life of food products and change their taste and appearance. The solution is: to encapsulate probiotics into double gel (bigel) systems made from food-grade ingredients, that provide system with a semi-solid texture compatible with various food products.
- Although bigels uploaded with probiotics are known, the life span of probiotic cells in this delivery system is not long enough to be conveniently used in food products in order to achieve more than $10^6$ CFU of viable probiotic bacteria in 1 g pf probiotic food. Therefore, it is important to pay special attention to preserving the viability of encapsulated probiotics for a longer period of time—up to 12 months. By combining probiotics with soluble dietary fibers extracted from berry pomace, which can serve as a prebiotic, it is possible to prolong the viability of probiotics cells in the developed bigel system.
- Another problem in the development of food-grade systems uploaded by probiotics is the lack of data on their scope to protect viable probiotic cultures under upper gastrointestinal tract conditions and release them in the colonic environment where complex microbiota is residing in order to achieve the expected beneficial effect to host health. The developed bigel system allows to keep probiotics viable and control their release in the targeted place of the gastrointestinal tract because of stable two-immiscible phase structure containing co encapsulated probiotic bacteria and prebiotic dietary fibers in hydrogel phase surrounded by oleogel phase.

DESCRIPTION OF DRAWINGS

The invention is explained in the drawings and diagrams. The drawings are provided as a reference to possible embodiments and experimental results and are not intended to limit the scope of the invention.

FIG. 7*a, b* depicts changes storage modulus (G') of bigels loaded with probiotics and bigels loaded with probiotics and prebiotic dietary fibers (a) after preparation and (b) after storage at −18 °C for 360 days.

Figure 1:
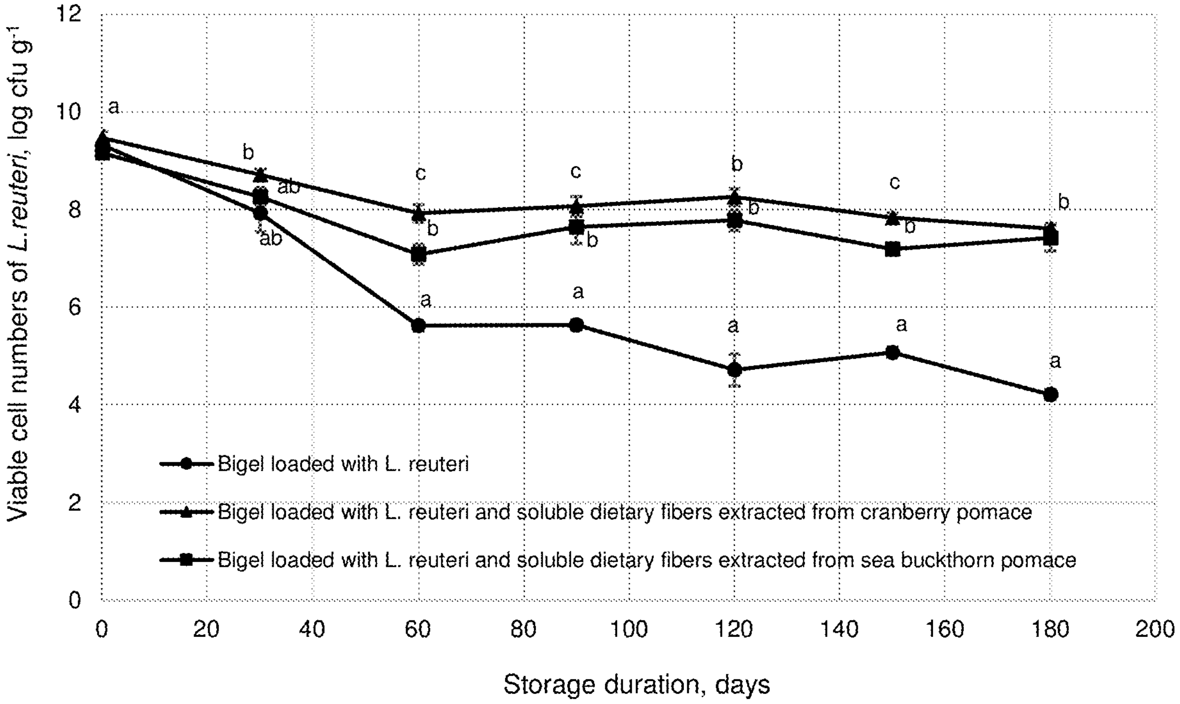
FIG. 1 depicts viability of *L. reuteri* cells during storage of bigels loaded with probiotics and prebiotic dietary fibers at +4 °C for 180 days with bigel loaded with probiotics alone as control.

A—non-probiotic butter spread product after storage at +4 °C for 150 days;

B—probiotic butter spread product after storage at +4 °C for 150 days;

C—non-probiotic butter spread product after storage at −18 °C for 150 days;

D—probiotic butter spread product after storage at −18 °C for 150 days.

DETAILED DESCRIPTION OF INVENTION

The description discloses food grade double-gel (bigel) system based on oleogel (vegetable oil and carnauba wax as gelator) and hydrogel (collagen) with co-encapsulated probiotics and prebiotic soluble dietary fibers extracted from berry pomace as structural approach for the delivery of sufficient amount of viable probiotic cells in butter spread products without changing their quality properties. Probiotic bacteria remain viable (above $10^7$ CFU/g) for 12 months in a bigel stored at −18 °C and 6 months in a bigel stored at +4 °C. Co-encapsulation of probiotics and prebiotics in bigel is mandatory for the viability of probiotics during storage at +4 °C and optional when stored at −18 °C. The distinctive feature of the developed bigel system is the capacity to protect viable probiotic cultures under upper gastrointestinal tract conditions and release them in the colonic environment where complex microbiota is residing in order to achieve the expected beneficial effect to host health.

Components of the bigel. The components listed below and their amounts compose one of the possible product embodiments developed and tested in the laboratory. However, the following components and their amounts do not limit the present invention, both in terms of the content of the materials and the proportions of the composition:

Distilled water;

Vegetable oil used for the oleogel formation;

Carnauba wax as gelator;

Collagen concentrate with 90% of protein for the hydrogel formation;

Suspension of probiotic cells (containing no less then $1.3\times10^{11}$ CFU/ml viable cells);

Soluble prebiotic dietary fiber extracted from berry pomace.

Preparing the soluble prebiotic dietary fiber from berry pomace. Fresh or defrosted berry pomace is dried to a moisture content of 7-9% by using various drying methods—hot air (35-40 °C, 48-72 hours), freeze-drying (−50 °C, 0.5 mbar, 24-48 hours). The dried pomace is cooled, weighed, and stored in sealed packages in a well-ventilated room with a relative humidity of no higher than 75% and an ambient temperature not exceeding 20 °C up to 4 months, or refrigerated at 4 °C up to 12 months. Before usage dry pomace is milled to 0.2-0.25 mm particles. Pomace powders are mixed with water in a ratio of 1:10, stirred for 10-15 min and centrifuged at 8000-10000 rev/sec for 15 min. The separated water-soluble fraction is mixed with ethanol in a ratio of 5:95 and stirred for 5-10 min. After filtering, the sediments are separated and dried by using various drying methods—hot air (35-40 °C, 48-72 hours), freeze-drying (−50 °C, 0.5 mbar, 24-48 hours).

Preparing the suspension of probiotic cells. The probiotic (*Lactobacillus reuteri*) strains were separately activated using MRS broth and incubated at 37 °C for 22 h aerobically. After incubation, the probiotic cells were obtained by centrifugation at 6000 rpm for 10 min at +4 °C and washed with sterile saline water. The obtained probiotic cell suspension contained no less than $1.3\times10^{11}$ cfu/ml of viable cells and was used in the bigel preparation.

Preparing the bigels: Two types of bigels (BI) are prepared:

Bigel loaded with probiotics in the hydrogel phase;

Bigel, loaded with probiotics and prebiotic dietary fibers in the hydrogel phase.

For this purpose, two types of water solutions for the hydrogel phase were produced:

60 g/100 g of collagen and dissolved in distilled water and incubated at 85 °C for 30 min continuously mixing (for the bigel loaded with probiotics);

60 g/100 g of collagen and 1.34 g/100 g of soluble dietary fiber dissolved in distilled water and incubated at 85 °C for 30 min continuously mixing (for the bigel loaded with probiotics and prebiotic dietary fibers).

For the oleogel phase 9 g/100 g of carnauba wax (as a gelator) was dissolved in vegetable oil and incubated at 85 °C for 30 min.

The resulting oil and water phases were homogenized in two stages. Firstly, oil and water phases were mixed at ratio 25:75 and homogenized for 60 s at 15 000 rpm maintaining the temperature at 85 °C. The mixture was cooled until 55 °C, 1 ml/100 g of pre-prepared probiotic suspension was added and the mixture was additionally homogenized at 11000 rpm for 60 s. Immediately after homogenization mixture was transferred to the ice bath in order to induce gelation of both phases and was stored at +4 °C or −18 °C.

Both prepared bigels contained 35.0 g/100 g of protein, 35.0 g/100 g of lipids and 29 g/100 g of water. These freshly prepared bigels were further used to prepare butter spread product.

Characteristics of the bigels. The following characteristics of prebiotic dietary fibers were examined:

The prebiotic activity of different probiotics paired with various soluble dietary fibers extracted from berry pomace or commercial prebiotic inulin (used as a control);

Kinetics of saccharide profile of various soluble dietary fibers extracted from berry pomace or commercial prebiotic inulin (used as a control) incubated with different probiotics.

Prebiotic activity (PA), reflects the ability of a given substrate to support the growth of an organism relative to other organisms and relative to growth on a non-prebiotic substrate, such as glucose. Therefore, dietary fibers containing carbohydrates can have a positive prebiotic activity score if they are metabolized as well as glucose by probiotic strains and are selectively metabolized by probiotics but not by other intestinal bacteria. The assay was performed according to Huebner et al. (2007) by adding 1% (vol/vol) of an overnight culture of each probiotic strain (*Lactobacillus plantarum* F1, *Lactobacillus reuteri* 182 or *Lactobacillus paracasei* subsp. *paracasei* ATCC® BAA-52) to separate tubes containing MRS Broth with 1% (wt/vol) glucose or 1% (wt/vol) soluble dietary fibers extracted from berry pomace or inulin (known as prebiotic and used as control). The cultures were incubated at 37 °C at ambient atmosphere. After 0 and 24 h of incubation, samples were enumerated on De Man, Rogosa (MRS), and Sharpe agar (Liofilchelm). In addition, overnight *E. coli* ATCC 25922 bacteria were added at 1% (vol/vol) to separate tubes containing M9 broth with 1% (wt/vol) glucose or 1% (wt/vol) prebiotic. The cultures were incubated at 37 °C at ambient atmosphere, and enumerated on Plate Count Agar (PCA, Liofilchelm) after 0 and 24 h of incubation. Each assay was replicated three times. The prebiotic activity score was determined using the following equation:

$$PA = \left[\frac{(\text{Probiotic } lg\ CFU/\text{ml on the prebiotic at 24 h} - \text{Probiotic } lg\ CFU/\text{ml on the prebiotic at 0 h}}{(\text{Probiotic } lg\ CFU/\text{ml on the glucose at 24 h} - \text{Probiotic } lg\ CFU/\text{ml on the glucose at 0 h})}\right] - \left[\frac{(E.coli\ lg\ CFU/\text{ml on the prebiotic at 24 h} - E.coli\ lg\ CFU/\text{ml on the prebiotic at 0 h}}{(E.coli\ lg\ CFU/\text{ml on the glucose at 24 h} - E.coli\ lg\ CFU/\text{ml on the glucose at 0 h})}\right]$$

Kinetics of saccharide profile of various soluble dietary fibers extracted from berry pomace or commercial prebiotic inulin (used as a control) was measured during their incubation with different probiotics (*Lactobacillus plantarum* F1, *Lactobacillus reuteri* 182 or *Lactobacillus paracasei* subsp. *paracasei* ATCC@ BAA-52). The samples were subjected to quantification of oligo- and mono- and disaccharides content after 0, 2, 4, 8, 12, 24, and 48 hours of incubation by size exclusion HPLC method. This involved dissolution of 10 mg of a freeze-dried sample in 1 mL of Millipore water (10 mg/mL). Analyses were performed in a Thermo Scientific Ultimate 3000 HPLC system coupled to a RefractoMax 521 refractive index detector (Thermo Fisher Scientific, Waltham, MA, USA). Saccharide components were separated using two size exclusion columns in series, Shodex SUGAR KS-802 and KS-801 (8.0 mmID×300 mm each (Showa Denko, Tokyo, Japan)), with ultrapure water as a mobile phase. The columns were operated at 80 °C with an isocratic flow rate of 0.5 mL/min, with a detector cell temperature of 60 °C. Samples were run for 60 min, and the injection volume was 10 μL. The total oligosaccharides were recorded as the sum of all the detected and quantified fractions of oligosaccharides with a degree of polymerization (DP) DP 7-10, DP 5-6, DP4, DP3, while the total mono- and disaccharides were recorded as a sum of the sucrose, glucose, fructose, sugar alcohols, and galacturonic acids. Quantification was achieved with external calibration curves of available standards or response factors. All chromatograms were recorded and processed using Chromeleon 7 software (Thermo Fisher Scientific, Waltham, MA, USA).

Characteristics of the bigels. The following characteristics of the bigels during storage at +4 °C for 6 months and −18 °C for 12 months were examined:

- physical stability,
- rheological properties,
- viability of probiotic cells.

Viability of probiotic cells during in vitro digestion of bigels was evaluated as well.

Rheological characteristics were evaluated by shear sweep and frequency sweep tests at 25 °C using a rheometer with a plate-to-plate system (diameter 20 mm, gap 2 mm).

The flow behaviour was estimated over a shear ranging from 0.01 to 500/s. Data were analyzed using the Herschel-Bulkley model, and the viscosity coefficient (K), and flow index (n) were calculated.

The limit of the linear viscoelastic (LVE) area was confirmed by the amplitude sweep test, before the frequency sweep test, and the shear strain value of 0.1% was determined for the LVE region. In the frequency sweep test, the storage (G') and loss moduli (G') were measured, and the angular frequency was changed from 0.1 to 100 rad/s at 25 °C.

Viability of probiotic cells was measured every month of the storage. The viable counts of *L. reuteri* were determined at all sampling points following EN ISO 15214:1998. 1 g of the bigel was weighed into a tube containing pre-warmed (37 °C) 9 ml of sterile saline water and serial dilutions were made so that the number of colonies per plate was between 15 and 300. The viable counts of *L. reuteri* were evaluated by the pour plating method of 1 ml of preparation in MRS Agar with Tween 80. All samples were plated in quadruplicate. The plated Petri plates were incubated in 37 °C temperature for 72 h. Viable cell numbers were calculated as log CFU/g.

Probiotic cells stability at each sampling point (upon production and throughout 180 days storage) was expressed as Δ log CFU/g, and calculated according to the equation:

$$\Delta \log CFU/g = \log CFU/g_{ti} - \log CFU/g_{t0}$$

where ti represents the viable cell numbers reported at each sampling time throughout storage and to represents the initial viable cell numbers reported at sampling time 0 days.

Simulated in vitro digestion was performed with the prepared bigels to evaluate the viability of probiotic cells during in vitro digestion under upper gastrointestinal tract conditions. The study was performed according to the static in vitro digestion protocol Infogest. Two test tubes one with 5 g of bigel containing co-encapsulated probiotics and prebiotics and another with the suspension of probiotic cells (as a control) were used to simulate the digestion in the mouth, stomach and small intestine. Samples to measure probiotic survival were withdrawn at the following times: initial, following the salivary phase (5 min, G5), at the end of the gastric phase (120 min, G120), the beginning of the intestinal phase (D120), mid-way through the intestinal phase (240 min, D240), and end of the intestinal phase (360 min, D360). Gastric phase samples were neutralized to pH 7.0±0.1, and the digestive process of intestinal phase samples was stopped by cooling in ice water to 0-4 °C. After the reaction was stopped, the amount of viable probiotic cells was determined.

A 1 gram sample was diluted in 9 mL sterile saline water (0.75% NaCl) according to EN ISO 15214:1998. To ensure accurate counts, the sample and saline water were shaken with a Vortex for 5 s. Serial dilutions were done, and enumeration was completed using a pour plate method. *L. reuteri* were grown aerobically on MRS agar with Tween 80 at 37 °C for 72 h. Viable cell numbers were calculated as $\log_{10}$ cfu/1 g.

Characteristics of the probiotic butter spread product made with BI. For the characterization of the probiotic butter spread product, it was made with bigel containing co-encapsulated probiotics and prebiotics and with probiotic cells suspension (as control). The following characteristics of the probiotic butter spread product were examined:

rheological properties, textural properties, viability of probiotic cells.

Rheological characteristics were evaluated by shear sweep and frequency sweep tests at 25 °C using a rheometer with a plate-to-plate system (diameter 20 mm, gap 2 mm) as described above.

The viability of probiotic cells was measured as described above.

Statistical analysis. All analyses were carried out in triplicate. The results are presented as the mean±standard deviation. A p-value of <0.05 was used to indicate significant differences between the mean values determined by an analysis of variance (ANOVA) using Statistica 12.0 (StatSoft, Inc., Oklahoma, AK, USA, 2013). For sensory evaluation, scores were submitted to the ANOVA with product, gender, and dysphagia (yes/no) as fixed factors and participants as random factor. Interactions were removed from the model as they were found to be not significant.

Results. The ability of soluble dietary fibers extracted from berry pomace to serve as prebiotics is described in several aspects: prebiotic activity score and kinetics of saccharide profile of various soluble dietary fibers extracted from berry pomace or commercial prebiotic inulin (used as a control) incubated with different probiotics. Quantitatively, the prebiotic activity score of different probiotics paired with soluble dietary fibers extracted from various berry pomace or commercial prebiotic inulin (used as a control) varied with the strains of organisms tested. Results are presented in Table 1. The highest values of prebiotic activity scores were reported to soluble dietary fibers extracted from lingonberry, cranberry and sea buckthorn pomace on *L. reuteri* (1.247±0.013, 1.214±0.029 and 1.035±0.009 respectively). The prebiotic activity scores of *L. plantarum* and *L. paracasei* paired with various soluble dietary fibers extracted from berry pomace were considerably lower than those indicated for *L. reuteri*. However, for these cells grown in a medium supplemented with soluble dietary fiber extracted from lingonberry and sea buckthorn pomace, the prebiotic activity scores were insignificantly higher or close to those determined for cells grown with inulin. It is very important that the PA scores of all tested soluble dietary fibers on *L. reuteri* were significantly (p>0.005) higher than that of commercial prebiotic inulin, indicating pairing soluble dietary fibers extracted from berry pomace with *L. reuteri* as an effective strategy for ensuring the viability of *L. reuteri* cells in an encapsulation system. The prebiotic activity scores for different berry pomaces and probiotic cells species are presented in Table 1.

TABLE 1

Prebiotic activity score of soluble dietary fibers extracted from berry pomace.

| Soluble dietary fibers extracted from berry pomace | Prebiotic activity score for different probiotics grown with soluble dietary fibers *L. reuteri* | *L. plantarum* | *L. paracasei* |
|---|---|---|---|
| Lingonberry | $1.247 \pm 0.013^d$ | $0.202 \pm 0.000^c$ | $0.210 \pm 0.001^c$ |
| Cranberry | $1.214 \pm 0.029^c$ | $0.060 \pm 0.002^a$ | $0.029 \pm 0.005^a$ |
| Sea buckthorn | $1.035 \pm 0.009^b$ | $0.114 \pm 0.008^b$ | $0.179 \pm 0.004^b$ |
| Inulin | $0.193 \pm 0.003^a$ | $0.103 \pm 0.022_b$ | $0.219 \pm 0.008^c$ |

Changes in the saccharide profile of soluble dietary fibers extracted from various berry pomace or commercial prebiotic inulin (used as a control) incubated with different probiotics for 48 hours were also measured (Table 2). Very similar kinetics of the saccharide profile were observed for all samples. Namely, a decrease of mono- and di-saccharides was determined after 24 h of incubation, while the amount of oligosaccharides remained unchanged. This means that the probiotic cells primarily used the mono- and di-saccharides from soluble dietary fiber as a carbon source for their activity. The remaining oligosaccharides will provide the carbon source needed for their activity, thus prolonging their viability. This is an important proof that enriching the environment of probiotic cells with soluble fibers extracted from berry pomace will prolong cells viability due to the presence of oligosaccharides, which the probiotic bacteria will be able to use as a carbon source for their activity. The saccharide profiles for different berry pomaces and probiotic cells species are presented in Table 2.

TABLE 2

Saccharide profile (mg/ml) of various soluble dietary fibers extracted from berry pomace or commercial prebiotic inulin (used as a control) incubated with different probiotics.

| Saccharides profile | Incubation duration 0 h | 2 h | 4 h | 8 h | 12 h | 24 h | 48 h |
|---|---|---|---|---|---|---|---|
| Soluble fiber extracted from lingonberry pomace with *L. reuteri* | | | | | | | |
| Σoligo | 28.8 | 27.8 | 27.3 | 28.3 | 24.3 | 27.9 | 27.6 |
| Σmono-di | 4.3 | 4.7 | 4.4 | 4.7 | 4.6 | 0.7 | 0.7 |
| Soluble fiber extracted from cranberry pomace with *L. reuteri* | | | | | | | |
| Σoligo | 30.8 | 30.0 | 27.6 | 29.6 | 26.0 | 29.4 | 27.9 |
| Σmono-di | 4.3 | 4.6 | 3.7 | 4.4 | 4.1 | 1.3 | 0.6 |
| Soluble fiber extracted from sea buckthorn pomace with *L. reuteri* | | | | | | | |
| Σoligo | 29.2 | 29.7 | 28.4 | 27.6 | 24.7 | 27.6 | 27.5 |
| Σmono-di | 3.2 | 3.9 | 3.3 | 3.1 | 3.7 | 0.9 | 0.7 |
| Inulin with *L. reuteri* | | | | | | | |
| Σoligo | 30.9 | 31.4 | 30.9 | 26.1 | 27.4 | 30.8 | 28.5 |
| Σmono-di | 2.2 | 2.8 | 3.4 | 2.7 | 3.1 | 0.7 | 0.6 |
| Soluble fiber extracted from lingonberry pomace with *L. plantarum* | | | | | | | |
| Σoligo | 61.6 | 64.3 | 50.9 | 50.6 | 64.7 | 68.4 | 69.7 |
| Σmono-di | 7.6 | 8.7 | 7.4 | 6.9 | 7.5 | 0.9 | 1.2 |
| Soluble fiber extracted from cranberry pomace with *L. plantarum* | | | | | | | |
| Σoligo | 68.7 | 69.3 | 60.0 | 61.1 | 63.1 | 69.1 | 68.5 |
| Σmono-di | 7.5 | 7.4 | 6.9 | 6.5 | 5.9 | 2.6 | 0.7 |
| Soluble fiber extracted from sea buckthorn pomace with *L. plantarum* | | | | | | | |
| Σoligo | 68.5 | 67.7 | 68.2 | 68.0 | 62.7 | 71.5 | 68.7 |
| Σmono-di | 6.2 | 6.0 | 7.8 | 7.4 | 4.8 | 3.2 | 1.3 |

TABLE 2-continued

| Saccharide profile (mg/ml) of various soluble dietary fibers extracted from berry pomace or commercial prebiotic inulin (used as a control) incubated with different probiotics. | | | | | | | |
|---|---|---|---|---|---|---|---|
| Saccharides | Incubation duration | | | | | | |
| profile | 0 h | 2 h | 4 h | 8 h | 12 h | 24 h | 48 h |
| Inulin with *L. plantarum* | | | | | | | |
| Σoligo | 75.2 | 71.2 | 73.3 | 69.1 | 71.9 | 76.0 | 74.8 |
| Σmono-di | 4.6 | 3.0 | 5.6 | 3.6 | 3.9 | 2.4 | 1.5 |
| Soluble fiber extracted from lingonberry pomace with *L. paracasei* | | | | | | | |
| Σoligo | 66.1 | 63.0 | 68.1 | 62.6 | 63.8 | 70.8 | 71.9 |
| Σmono-di | 9.4 | 8.8 | 44.3 | 8.9 | 9.4 | 1.8 | 2.6 |
| Soluble fiber extracted from cranberry pomace with *L. paracasei* | | | | | | | |
| Σoligo | 68.2 | 66.4 | 67.0 | 65.1 | 64.1 | 72.4 | 67.3 |
| Σmono-di | 7.0 | 6.9 | 9.0 | 7.9 | 6.9 | 2.8 | 1.4 |
| Soluble fiber extracted from sea buckthorn pomace with *L. paracasei* | | | | | | | |

during storage for 6 months at +4 °C are presented in FIG. 1. In the initial time point, the viable cell numbers of all tested samples varied between 9.15 and 9.46 log CFU/g. Throughout the storage period up to 180 days, *L. reuteri* viable cell numbers were found to be 7.41 and 7.61 log CFU/g (FIG. 1) when they were loaded into bigels together with prebiotic dietary fibers. Whereas, in bigel loaded only with *L. reuteri* cells and stored at the same conditions, the viable cells numbers were detected at the level 4.21 log CFU/g. Bigels loaded with *L. reuteri* together with prebiotic dietary fibers had significantly lower log cycle reduction by 180 days of storage in comparison with bigels loaded only with *L. reuteri* (Table 3). Meanwhile, bigels loaded with *L. reuteri* cells were less stable over storage registering >5 log cycle reduction by 180 days of storage. So, co-encapsulation of *L. reuteri* cells and prebiotic dietary fibers extracted from berry pomace in bigel system had positive effect on the viability of probiotic cells during storage for 6 months at +4 °C. The results of this effect are presented in Table 3.

TABLE 3

| Fluctuation in viable *L. reuteri* cell numbers during storage of bigels loaded with probiotics and bigels loaded with probiotics and prebiotic dietary fibers at +4 °C for 180 days. | | | | | | |
|---|---|---|---|---|---|---|
| Bigels | Δ viable cell numbers after storage for | | | | | |
| sample | 30 days | 60 days | 90 days | 120 days | 150 days | 180 days |
| 1 | $-1.40 \pm 0.00^{aE}$ | $-3.70 \pm 0.02^{aD}$ | $-3.69 \pm 0.08^{aD}$ | $-4.61 \pm 0.36^{aB}$ | $-4.25 \pm 0.03^{aC}$ | $-5.11 \pm 0.12^{aA}$ |
| 2 | $-0.75 \pm 0.13^{bE}$ | $-1.54 \pm 0.06^{cB}$ | $-1.40 \pm 0.05^{bC}$ | $-1.21 \pm 0.08^{bD}$ | $-1.64 \pm 0.02^{cB}$ | $-1.85 \pm 0.03^{bA}$ |
| 3 | $-0.90 \pm 0.05^{bF}$ | $-2.08 \pm 0.05^{bA}$ | $-1.52 \pm 0.04^{bD}$ | $-1.38 \pm 0.02^{bE}$ | $-1.97 \pm 0.01^{bB}$ | $-1.74 \pm 0.03^{bc}$ |

1—Bigel loaded with probiotic cells;

2—Bigel loaded with probiotic cells and prebiotic dietary fiber extracted from cranberry pomace;

3—Bigel loaded with probiotic cells and prebiotic dietary fiber extracted from sea buckthorn pomace. Lower case letters indicate significant ($p < 0.05$) differences between different bigel samples and upper case letters indicate significant ($p < 0.05$) differences during storage TABLE 2-continued

| Saccharide profile (mg/ml) of various soluble dietary fibers extracted from berry pomace or commercial prebiotic inulin (used as a control) incubated with different probiotics. | | | | | | | |
|---|---|---|---|---|---|---|---|
| Saccharides | Incubation duration | | | | | | |
| profile | 0 h | 2 h | 4 h | 8 h | 12 h | 24 h | 48 h |
| Σoligo | 68.7 | 66.0 | 66.7 | 64.9 | 63.6 | 68.5 | 65.2 |
| Σmono-di | 6.9 | 6.5 | 7.7 | 6.8 | 6.1 | 3.1 | 1.0 |
| Inulin with *L. paracasei* | | | | | | | |
| Σoligo | 75.2 | 73.0 | 74.5 | 71.3 | 69.1 | 61.4 | 76.4 |
| Σmono-di | 3.8 | 4.6 | 3.9 | 4.0 | 3.8 | 1.6 | 1.7 |

According to our results, we can reasonably say that soluble dietary fibers extracted from berry pomace have a prebiotic effect and the addition of them to the environment of probiotic cells can be used as an effective strategy for ensuring the viability of cells in an encapsulation system.

To use soluble dietary fibers extracted from berry pomace loaded together with probiotic bacteria in the double gel system, the bigel containing *L. reuteri* and soluble fiber extracted from berry pomace in the hydrogel phase was produced. As a control the bigel containing *L. reuteri* in the hydrogel phase was produced. Physical stability, rheological properties of bigel and viability of loaded *L. reuteri* cells were examined during storage of loaded bigel at +4 °C and −18 °C.

Figure 2:
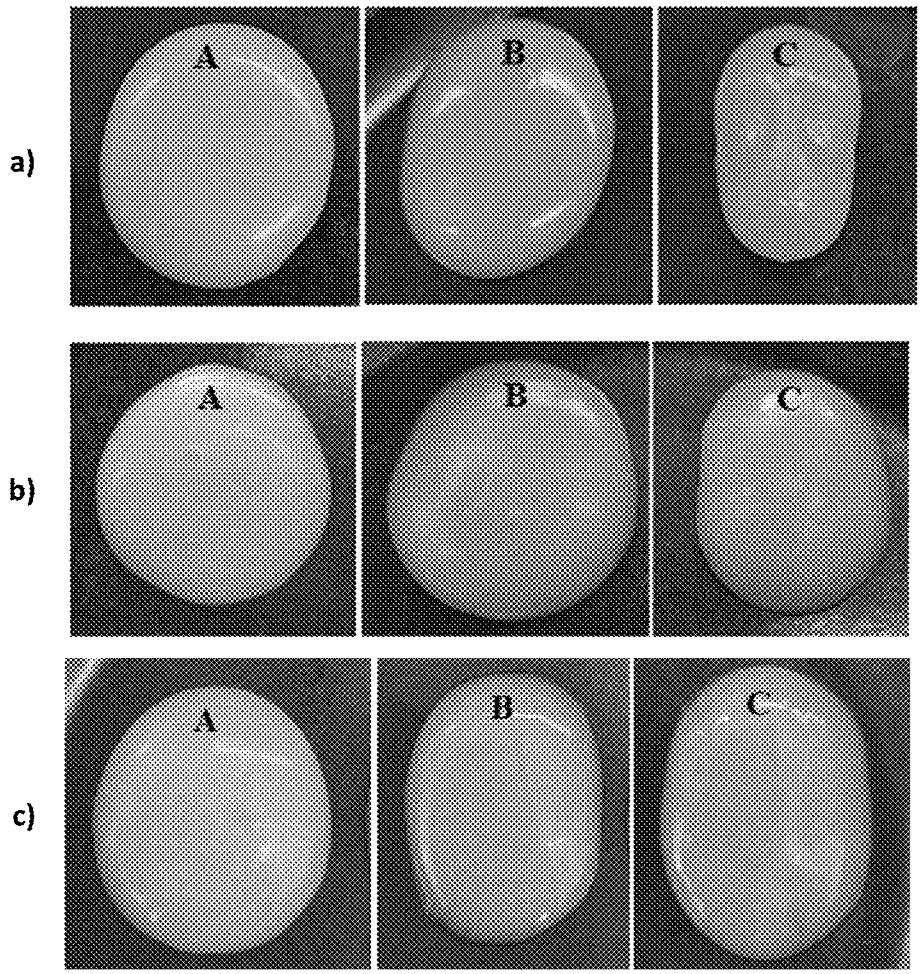
FIG. 2*a, b, c* depicts appearance of bigels loaded with probiotics and bigels loaded with probiotics and prebiotic dietary fibers (a) after preparation; (b) after storage at +4 °C for 180 days; and (c) after storage at −18 °C for 360 days: A—Control-bigel loaded with *L. reuteri*; B—Bigel loaded with *L. reuteri* and soluble fibers extracted from sea buckthorn pomace; C—Bigel loaded with *L. reuteri* and soluble fibers extracted from cranberry pomace.
Figure 3:
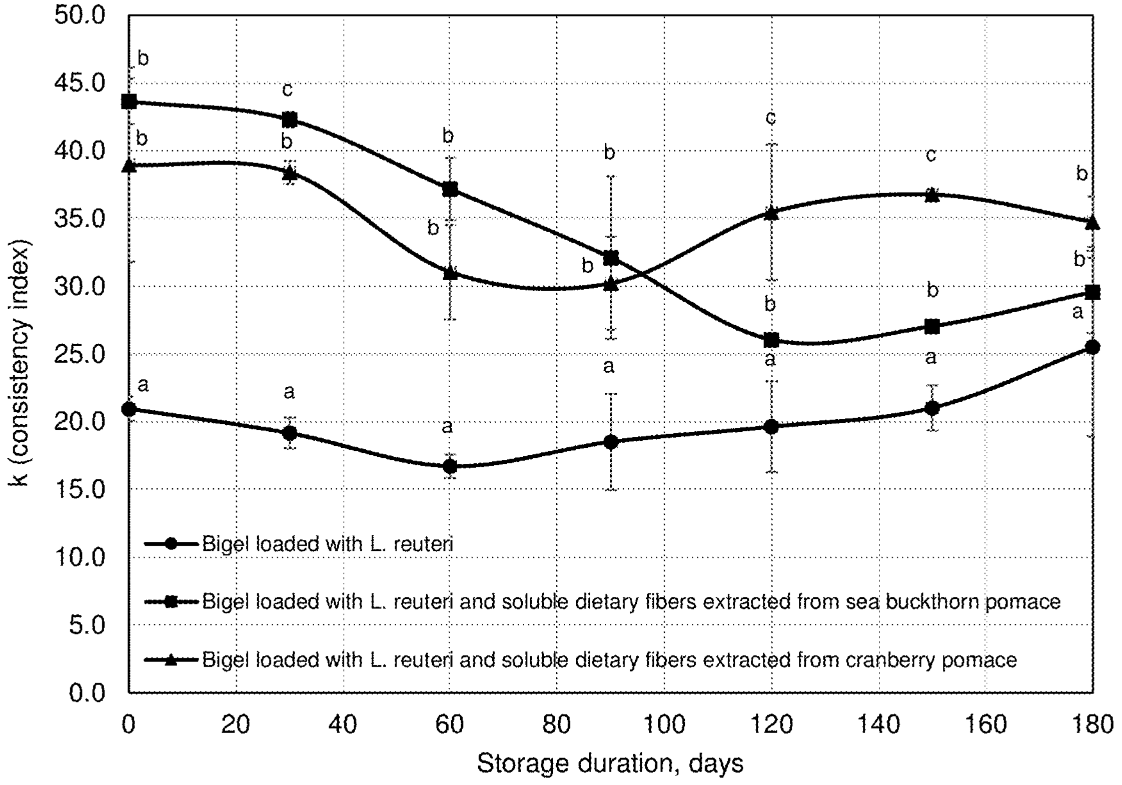
FIG. 3 depicts changes in consistency index of bigels loaded with probiotics and bigels loaded with probiotics and prebiotic dietary fibers during storage at +4 °C for 180 days.
Figure 4:
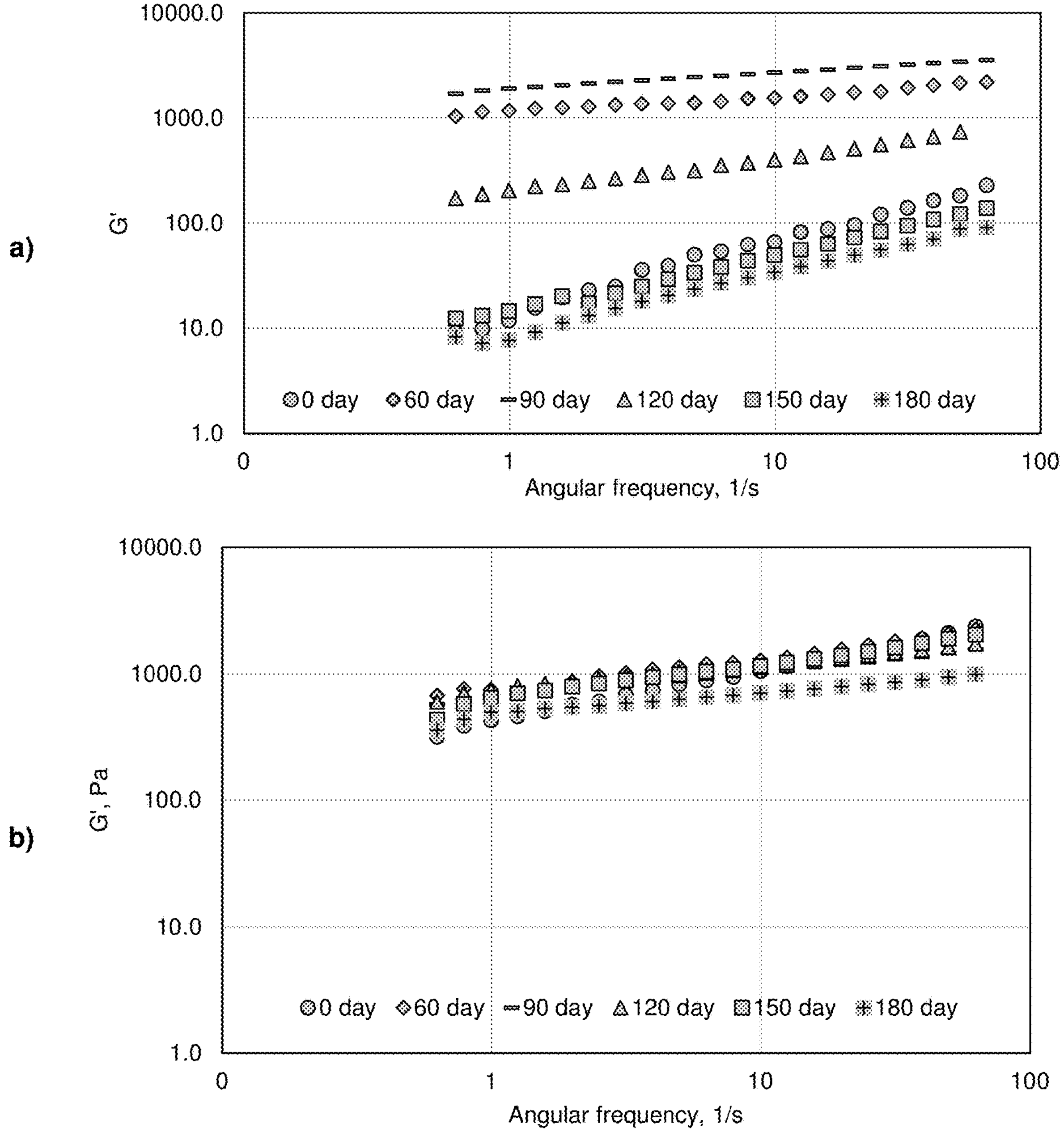
FIG. 4*a, b* depicts changes storage modulus (G') of (a) bigels loaded with probiotics and (b) bigels loaded with probiotics and prebiotic dietary fibers during storage at +4 °C for 180 days (b).

*L. reuteri* viable cell numbers in bigels loaded with cells and prebiotic dietary fibers extracted from berry pomace In order to evaluate the possibilities of using bigels loaded with probiotics and prebiotic dietary fibers in probiotic food products, their physical stability and rheological properties were determined during storage. From the pictures presented in FIG. 2 it can be seen that all bigels were able to support their own weight (did not flow when inverted). Bigel loaded with probiotics had an off-white color, bigels loaded with probiotics and prebiotic dietary fibers color was with a slightly brownish shadow depending on the soluble dietary fibers extracted from different types of berry pomace. The appearance of the bigels remained unchanged during the entire storage period. The rheological properties of bigels were explored by flow and viscoelastic behavior studies to provide insight into their utility for food application and stability during storage. The obtained results were shown in FIGS. 3 and 4. The consistency indices of bigel loaded with probiotics were lower than those of bigels loaded with probiotics and prebiotic dietary fibers and remained almost the same during the whole storage period indicating that all tested bigels displayed adequate stability. The storage modulus G' of all tested bigels tended to increase with frequencies (0.1 to 100 rad/s) and the bigels were frequency-dependent during the whole period of storage. It was found that G' of bigels loaded with probiotics and prebiotic dietary fibers remained similar throughout the 6 months of storage, while the G' values of bigels loaded with probiotics alone differed significantly during storage. Such results testify to the positive influence of probiotic dietary fibers on the stability of bigels when they are co-encapsulated in the hygrogel phase of bigels together with probiotic bacteria.

Figure 5:
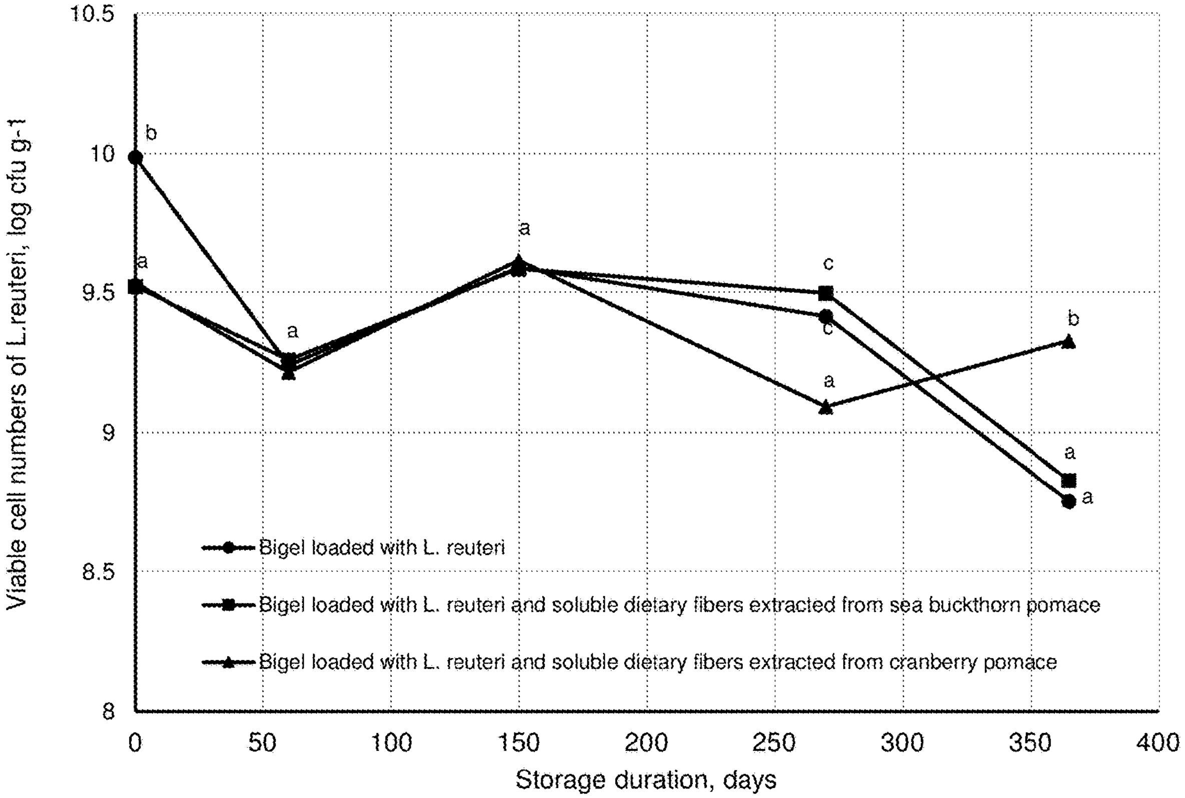
FIG. 5 depicts viability of *L. reuteri* cells during storage of bigels loaded with probiotics and prebiotic dietary fibers at −18 °C for 360 days with bigel loaded with probiotics alone as control.

While keeping the bigels at −18 °C, we conducted their research for 360 days. As before, we studied the viability of probiotic bacteria and their rheological properties changes. FIG. 5 presents *L. reuteri* cells that were loaded alone or together with prebiotic dietary fibers in the bigels during storage at −18 °C for 360 days. In the initial time point, there were no significant variability in the cell numbers loaded in all bigels and they were in the range 9.5-10.0 log cycles. The counts of *L. reuteri* bacteria were found to be on the same line at the final sampling point (between 8.75 and 9.33 log CFU/g). Additionally, *L. reuteri* cells remained relatively stable during storage at −18 °C registering <1 log cycle reduction by 270 days of storage for bigels loaded with probiotics only and 360 days of storage for bigels loaded with probiotics and prebiotic dietary fibers (Table 4). So, co-encapsulation of *L. reuteri* cells and prebiotic dietary fibers extracted from berry pomace in bigel system had no positive effect on the viability of probiotic cells during storage for 12 months at −18 °C.

TABLE 4

Fluctuation in viable *L. reuteri* cell numbers during storage of bigels loaded with probiotics and bigels loaded with probiotics and prebiotic dietary fibers at −18 °C for 360 days.

| | Δ viable cell numbers after storage for | | | |
|---|---|---|---|---|
| Bigels sample | 60 days | 150 days | 270 days | 360 days |
| 1 | −0.75 ± 0.00$^{aB}$ | −0.40 ± 0.06$^{aD}$ | −0.57 ± 0.09$^{aC}$ | −1.27 ± 0.00$^{aA}$ |
| 2 | −0.32 −± 0.01$^{bB}$ | 0.08 ± 0.04$^{bD}$ | −0.44 ± 0.03$^{aA}$ | −0.20 ± 0.03$^{cC}$ |
| 3 | −0.26 ± 0.07$^{bB}$ | 0.06 ± 0.03$^{bD}$ | −0.02 ± 0.06$^{bC}$ | −0.68 ± 0.01$^{bA}$ |

1—Bigel loaded with probiotic cells;

2—Bigel loaded with probiotic cells and prebiotic dietary fiber extracted from cranberry pomace;

3—Bigel loaded with probiotic cells and prebiotic dietary fiber extracted from sea buckthorn pomace. Lower case letters indicate significant ($p < 0.05$) differences between different bigel samples and upper-case letters indicate significant ($p < 0.05$) differences during storage.

Figure 6:
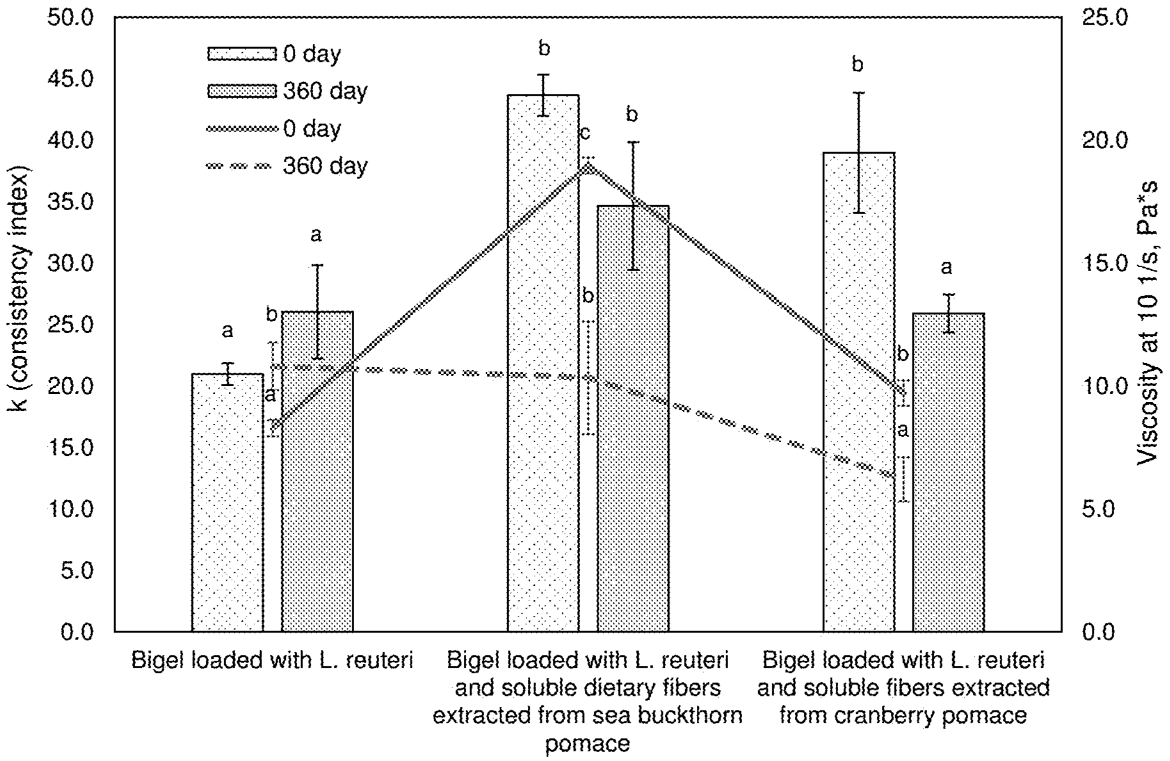
FIG. 6 depicts changes in consistency index and viscosity of bigels loaded with probiotics and bigels loaded with probiotics and prebiotic dietary fibers during storage at −18 °C for 360 days.

Bigel systems encounter the problem of less structural stability during storage at low temperatures. In order to evaluate whether these systems can be used as a carrier of probiotic bacteria in food products, it is necessary to determine their structural stability during storage. We did this by comparing the flow and viscoelastic properties of bigels loaded with probiotics alone and bigels loaded with probiotics and prebiotic dietary fibers immediately after production and after storage at −18 °C for 360 days. The obtained results are shown in FIGS. 6 and 7. It was observed that Consistency index and viscosity slightly increased for bigels loaded with probiotics and slightly decreased for bigels loaded with probiotics and prebiotic dietary fibers during storage for 360 days at −18 °C. The differences in storage modulus G' of tested bigels were more pronounced at the very beginning of storage. After 360 days of storage the values of G' were at the same range for all tested bigels. These data lead to the conclusion that regardless of the filling of the bigels, their structure remained stable during the entire period of storage at a temperature of −18 °C, which was also confirmed by the appearance of the bigels. In FIG. 2*c*, we can see that after 360 days of storage at low temperatures, their appearance remained unchanged.

It is well established that food grade double-gel system based on oleogel and hydrogel with co-encapsulated probiotics and prebiotic soluble dietary fibers extracted from berry pomace is favourable for the delivery of sufficient amount of viable probiotic cells without changing structural stability of bigel during storage. Probiotic bacteria remain viable (above $10^7$ CFU/g) for 12 months in a bigel stored at −18 °C and 6 months in a bigel stored at +4 °C. Co-encapsulation of probiotics and prebiotics in bigel is mandatory for the viability of probiotics during storage at +4 °C and optional when stored at −18 °C.

Figure 8:
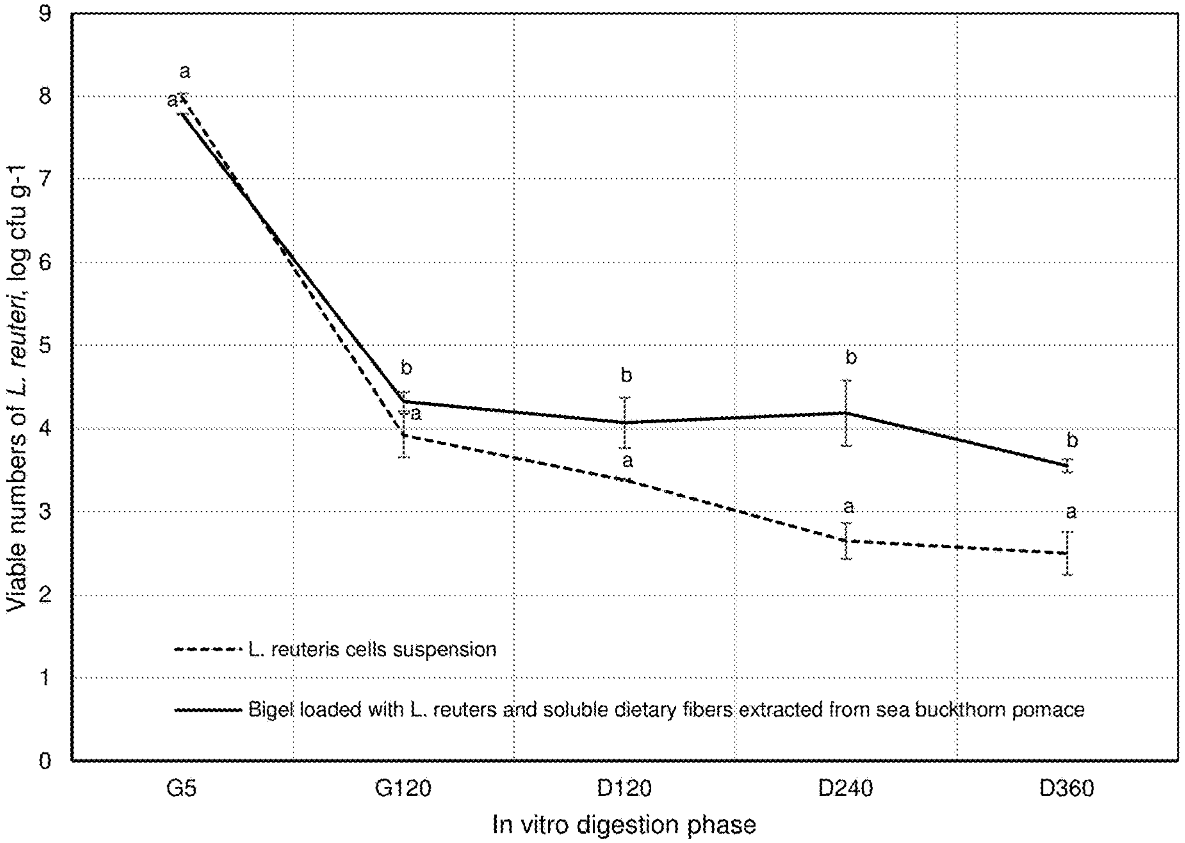
FIG. 8 depicts *L. reuters* viability at various digestion time points.

To prove that bigel loaded with probiotics and prebiotic dietary fibers is capable to protect viable probiotic cultures under upper gastrointestinal tract conditions and release them in the colonic environment where complex microbiota is residing digestive degradation of the bigels loaded with probiotics and prebiotic dietary fibers was analysed. We evaluated the survival of co-encapsulated *L. reuteri* cells together with prebiotic dietary fibers throughout in vitro digestion. As a control, the suspension of *L. reuteri* cells was used in this experiment. Free *L. reuteri* cells and those encapsulated in bigel system showed similar trends in viability throughout in vitro digestion, with decreasing viability as digestion progressed (FIG. 8). In the gastric phase, the same behavior of *L. reuteri* bacteria was recorded registering no significant variation in bacteria numbers at the beginning of the gastric stage (point G5) and around 4 log cycle reduction at the end of gastric stage (point G120), regardless of the matrix. The low survival of probiotic bacteria during the gastric phase was observed and it was obvious that the bigel system insufficiently protected the cells from degradation under acidic conditions (pH2). Although it should be stated that a slightly higher number of viable bacteria was recorded at this point in case of encapsulated *L. reuteri* cells. Upon reaching the intestinal phase probiotic cells numbers were higher in bigel system than that in the not protected bacteria suspension. Further in the intestinal phase (mid-way point D240 and end of the intestinal phase point D360), the viability of non-protected *L. reuteri* cells decreased while protected bacteria remained stable. Apparently, by encapsulating the bacteria in the bigel, it was possible to protect them from the lethal effects of the bile acids present in the intestine. Overall, the results showed there was no significant difference in *L. reuteri* cells viability during the gastric stage of digestion when they were uploaded into the bigel system versus non-protected bacteria. However, a trend of higher probiotic viability was recorded in bigels uploaded with *L. reuteri* cells and prebiotic dietary fibers compared to non-protected probiotics during the intestinal phase of in vitro digestion. Such results lead to the conclusion that the developed bigel system allows to keep probiotics viable under upper gastrointestinal tract conditions because of stable two-immiscible phase structure containing co encapsulated probiotic bacteria and prebiotic dietary fibers in hydrogel phase surrounded by oleogel phase.

In order to find out whether bigel could be used as a carrier of probiotic bacteria in the production of probiotic products, a probiotic butter spread product with the developed bigel loaded with *L. reuteri* cells and prebiotic dietary fibers extracted from sea buckthorn pomace was produced. The probiotic butter spread product was stored under different conditions and the number of viable *L. reuteri* cells, storage modulus G and hardness were determined monthly. Non-probiotic butter spread product (without bigel loaded with probiotics and prebiotic dietary fibers) was used as a control. Results are presented in Table 5.

The number of probiotic bacteria in the product is a crucial index for qualifying the product as a probiotic. According to the results of our experiment, the number of probiotic cells was 8.3 log CFU/g at the beginning of storage. The survival of *L. reuteri* cells in the butter spread product depended on the conditions of storage. When the butter spread product was stored at +4 °C, the viable cell number decreased gradually and was 7.1+0.2 log CFU/g after 2 months of storage thus meeting the required 6 log CFU/g for a functional probiotic food product. Further storage of the butter spread product resulted in the reduction of probiotics to a level where the product cannot be classified as a probiotic product. Different trends in bacterial viability were observed when the butter spread product was stored at −18 °C. During the entire product storage period of 5 months, the number of probiotic bacteria decreased slightly to 7.4 log CFU/g. So, according to existing requirements, the product remained probiotic during the entire storage period.

The rheological and textural properties of the butter spread products stored in a refrigerator (+4 °C) and in a freezer (−18 °C) were monitored at 30-day intervals for 5 months. As the storage time was increased, the results showed imperceptible changes of storage modulus G' for both butter spread products regardless of the storage temperature. The trends in hardness changes during storage were also similar for both butter spread products. During the first 2 months of storage, the hardness increased and began to decrease during further storage, reaching the values determined at the beginning of storage. The results presented in Table 5.

TABLE 5

Changes of probiotic and non-probiotic butter spread product during storage at +4 °C and −18 °C

| | Control - butter spread product | | | | | | Probiotic butter spread product made with bigel loaded with probiotics and prebiotic dietary fibers | | | | | |
|---|---|---|---|---|---|---|---|---|---|---|---|---|
| | 0 | 1 | 2 | 3 | 4 | 5 | 0 | 1 | 2 | 3 | 4 | 5 |
| | Storage at +4 °C for months | | | | | | | | | | | |
| Viable cell numbers of *L. reuteri*, log CFU/g | n* | n* | n* | n* | n* | n* | 8.3 ± $0.1^{e}$ | 7.7 ± $0.1^{d}$ | 7.1 ± $0.2^{c}$ | 5.6 ± $0.1^{b}$ | 5.1 ± $0.1^{a}$ | 4.9 ± $0.2^{a}$ |
| Storage modulus G', Pa $\cdot 10^{5}$, at 1 Hz, | 1.64 ± $0.04^{b}$ | 1.28 ± $0.12^{a}$ | 1.81 ± $0.03^{bcd}$ | 1.78 ± $0.05^{bcd}$ | 1.85 ± $0.17^{d}$ | 1.85 ± $0.03^{cd}$ | 1.49 ± $0.08^{ab}$ | 1.55 ± $0.30^{ab}$ | 1.48 ± $0.07^{ab}$ | 1.55 ± $0.07^{ab}$ | 1.57 ± $0.04^{b}$ | 1.52 ± $0.01^{ab}$ |
| Hardness, N | 8.8 ± $1.4^{a}$ | 20.2 ± $1.4^{c}$ | 20.2 ± $1.5^{c}$ | 14.6 ± $1.6^{d}$ | 16.6 ± $1.6^{f}$ | 15.6 ± $1.7^{e}$ | 6.1 ± $0.8^{a}$ | 14.2 ± $3.2^{d}$ | 13.8 ± $1.7^{d}$ | 10.3 ± $1.1^{b}$ | 8.9 ± $1.3^{ab}$ | 8.1 ± $0.9^{ab}$ |
| | Storage at −18 °C for months | | | | | | | | | | | |
| Viable cell numbers of *L. reuteri*, log cfu g−1 | n* | n* | n* | n* | n* | n* | 8.3 ± $0.1^{b}$ | n* | 8.1 ± $0.1^{b}$ | n* | 7.4 ± $0.1^{a}$ | 7.4 ± $0.0^{a}$ |
| Storage modulus G', Pa $\cdot 10^{5}$, at 1 Hz, | 1.64 ± $0.04^{bc}$ | 1.39 ± $0.07^{a}$ | 1.75 ± $0.08^{c}$ | 1.70 ± $0.16^{ab}$ | 1.70 ± $0.00^{bc}$ | 1.74 ± $0.09^{bc}$ | 1.49 ± $0.08^{ab}$ | 1.55 ± $0.17^{b}$ | 1.48 ± $0.09^{ab}$ | 1.35 ± $0.02^{ab}$ | 1.36 ± $0.09^{ab}$ | 1.32 ± $0.10^{a}$ |
| Hardness, N | 8.8 ± $1.4^{a}$ | 16.2 ± $0.9^{c}$ | 18.4 ± $2.1^{d}$ | 9.7 ± $1.5^{ab}$ | 11.5 ± $1.0^{b}$ | 10.5 ± $0.8^{ab}$ | 6.1 ± $0.8^{ab}$ | 10.0 ± $0.8^{c}$ | 14.7 ± $2.5^{d}$ | 7.8 ± $0.4^{bc}$ | 6.9 ± $0.3^{ab}$ | 5.3 ± $0.8^{a}$ |

Lower case letters indicate significant ($p < 0.05$) differences during storage.

Figure 9:
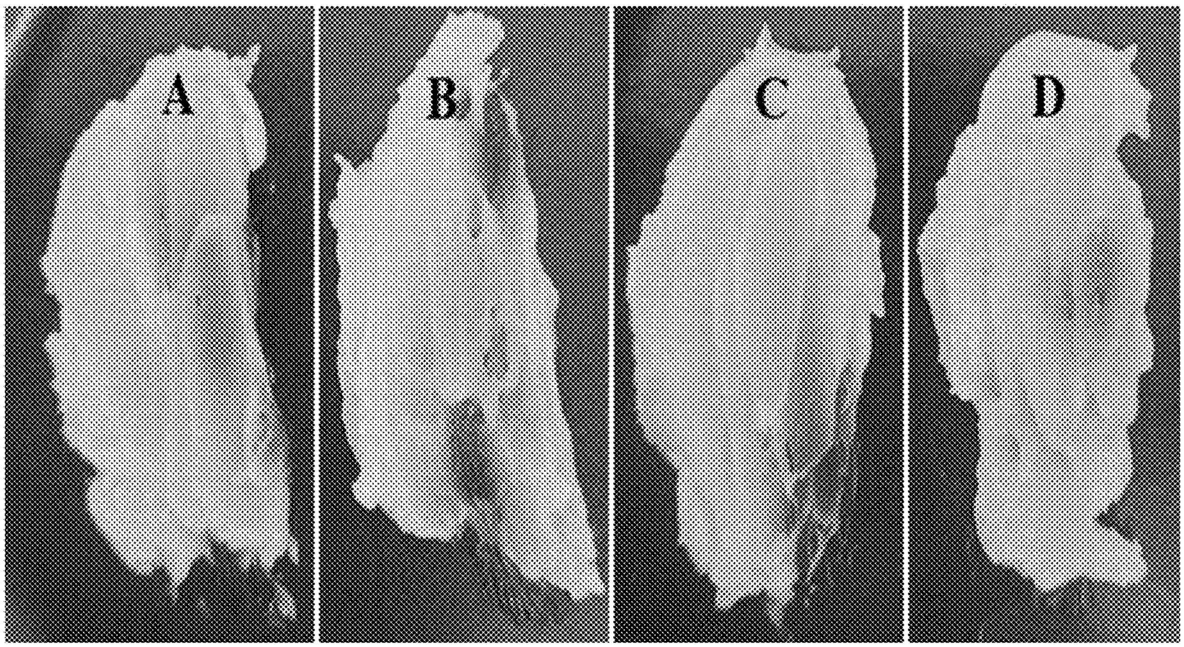
FIG. 9A,B,C,D depicts the appearance of butter spread products.

These results confirm that bigels loaded with *L. reuteri* cells and prebiotic dietary fibers provide protection to the probiotic bacteria and do not affect the appearance (FIG. 9) and texture of the food made with these bigels.

Non-Patent Literature

[1] FAO/WHO. (2002). Guidelines for the Evaluation of Probiotics in Food. *Report of a Joint FAO/WHO Working Group on Drafting Guidelines for the Evaluation of Probiotics in Food.* www.fao.org/es/ESN/Probio/probio.htm.

[2] Razavi, S., S. Janfaza, N. Tasnim, D. L. Gibson & M. Hoorfar. (2021). Microencapsulating polymers for probiotics delivery systems: Preparation, characterization, and applications. *Food Hydrocolloids,* 120, Article 106882.

[3] Frakolaki, G., V. Giannou, D. Kekos, & C. Tzia. (2021). A review of the microencapsulation techniques for the incorporation of probiotic bacteria in functional foods. *Critical Reviews in Food Science and Nutrition,* 61(9), Article 1515-1536.

[4] Shori, A. B. (2015). The potential applications of probiotics on dairy and non-dairy foods focusing on viability during storage. *Biocatalysis and Agricultural Biotechnology,* 4(4), Article 423-431.

[5] de Vos, P., Faas, M. M., Spasojevic, M., & Sikkema, J. (2010). Encapsulation for preservation of functionality and targeted delivery of bioactive food components. *International Dairy Journal,* 20(4), Article 292-302.

[6] Van Baarlen, P. F. J., Troost, S., Van Hemert, C., Van Der Meer, W. M., de Vos, P. J., de Groot, G. J. E. J., Hooiveld, R. J. M., Brummer, R. J., & Kleerebezem. M. (2009). Differential NF-B pathways induction by *Lactobacillus plantarum* in the duodenum of healthy humans correlating with immune tolerance. *Proceedings of the National Academy of Sciences of the United States of America* (PNAS), 106(7), Article 2371-2376.

[7] Martins, A., Cerqueira, M., Fasolin, L., Cunha, R., & Vicente, A. (2016). Beeswax organogels: Influence of gelator concentration and oil type in the gelation process. *Food Research International* 84, Article 170-179.

[8] Singh, V. K., Qureshi, D., Nayak, S. K., & Pal, K. (2018). Bigels. In *Polymeric gels* (pp. 265-282), Book Chapter, Woodhead Publishing.

[9] Angelerou, M. G. F., Markus, R., Paraskevopoulou, V., Foralosso, R., Clarke, P., Alvarez, C., Chenlo, M., Angel, M., Johnson, L., Rutland, C., Allen, S., Brasnett, C., Seddon, A., Zelzer, M., & Marlow, M. (2020). Mechanistic investigations into the encapsulation and re-lease of small molecules and proteins from a supramolecular nucleoside gel in vitro and in vivo. *Journal of Controlled Release,* 317, Article 118-129.

[10] Chen, H., Dai, H., Zhu, H., Ma, L., Fu, Y., Feng, X., & Sun, Y., Zhang, Y. (2021). Construction of dual-compartmental micro-droplet via shrimp ferritin nanocages stabilized Pickering emulsions for co-encapsulation of hydrophobic/hydrophilic bioactive compounds. *Food Hydrocolloids,* 126, Article 107443.

[11] Okonkwo, C. E., Ofoedu, C. E., Hussain, S. Z., Adeyanju, A. A., Naseer, B., Inyinbor, A. A., Olaniran, A. F., & Kamal-Eldin, A. (2022). Application of biogels for bioactives delivery: Recent developments and future research insights. *Applied Food Research,* 2, Article 100238.

[12] Zheng, H., Mao, L., Cui, M., Liu, J., & Gao, Y. (2020). Development of food-grade bigels based on κ-carrageenan hydrogel and monoglyceride oleogels as carriers for β-carotene: Roles of oleogel fraction. *Food Hydrocolloids,* 105, Article 105855.

[13] Liu, K., Huang, R. L., Zha, X. Q., Li, Q. M., Pan, L. H., & Luo, J. P. (2020). Encapsulation and sustained release of curcumin by a composite hydrogel of lotus root amylopectin and chitosan. *Carbohydrate Polymers,* 232, Article 115810.

[14] Martinez, R. M., Magalhães, W. V., da Silva Sufi, B., Padovani, G., Nazato, L. I. S., Velasco, M. V. R., Lannes, S. C. D. S., & Baby, A. R. (2021). Vitamin E-loaded bigels and emulsions: Physicochemical characterization and potential biological application. *Colloids and Surfaces B: Biointerfaces,* 201, Article 111651.

[15] Mousavi, S. N., Hosseini, E., Dorraji, M. S. S., Mohammadi, S. S., Pourmansouri, Z., Ra-soulifard, M. H., Doosti, M., & Chiti, H. (2021). Synthesis of a green bigel using cottonseed oil/cannabis oil/alginate/ferula gum for quercetin release: Synergistic effects for treating infertility in rats. *International Journal of Biological Macromolecules,* 177, Article 157-165

[16] Zhu, Q., Gao, J., Han, L., Han, K., Wei, W., Wu, T., Li, J., & Zhang, M. (2021). Development and characterization of novel bigels based on monoglyceride-beeswax oleogel and high acyl gellan gum hydrogel for lycopene delivery. *Food Chemistry,* 365, Article 130419.

[17] Behera, B., Sagiri, S., Singh, V. K., Pal, K., & Anis, A. (2014). Mechanical properties and delivery of drug/probiotics from starch and non-starch based novel bigels: A comparative study. Starch-Stärke, 66(9-10), Article 865-879.

[18] Zhuang, X., Clark, S., & Acevedo, N. (2021). Bigels—oleocolloid matrices—as probiotic protective systems in yogurt. *Journal of Food Science,* 86(11), Article 4892-4900.

[19] Bollom, M. A., Clark, S., & Acevedo, N. C. (2021). Edible lecithin, stearic acid, and whey protein bigels enhance survival of probiotics during in vitro digestion. *Food Bioscience,* 39, Article 100813.

[20] Gibson, G. R., Hutkins, R., Sanders, M. E., Prescott, S. L., Reimer, R. A., Salminen, S. J., Scott, K., Stanton, C., Swanson, K. S., Cani, P. D., Verbeke, K., & Reid, G. (2017). Expert consensus document: The International Scientific Association for Probiotics and Prebiotics (ISAPP) consensus statement on the definition and scope of prebiotics. *Nature reviews Gastroenterology & hepatology,* 14(8), Article 491-502.

[21] Lordan, C., Thapa, D., Ross, R. P., & Cotter, P. D. (2020). Potential for enriching next-generation health-promoting gut bacteria through prebiotics and other dietary components. *Gut Microbes,* 11(1), Article 1-20.

[22] Augustin, L. S. A., Aas, A. M., Astrup, A., Atkinson, F. S., Baer-Sinnott, S., Barclay, A. W., Brand-Miller, J. C., Brighenti, F., Bullo, M., Buyken, A. E., Ceriello, A., Ellis, P. R., Ha, M. A., Henry, J. C., Kendall, C. W. C., La Vecchia, C., Liu, S., Livesey, G., Poli, A., Salas-Salvadó, J., Riccardi, G., Riserus, U., Rizkalla, S. W., Sievenpiper, J. L., Trichopoulou, A., Usic, K., Wolever, T. M. S., Willett, W. C., & Jenkins, D. J. A. (2020). Dietary fibre consensus from the international carbohydrate quality consortium (ICQC). *Nutrients,* 12, Article 2553.

[23] Espitia, P. J. P., Batista, R. A., Azeredo, H. M. C., & Otoni, C. G. (2016). Probiotics and their potential applications in active edible films and coatings. *Food Research International,* 90, Article 42-52.

[24] Sathyabama, S., Ranjith kumar, M., Bruntha devi, P., Vijayabharathi, R., & Brindha priyadharisini, V. (2014). Co-encapsulation of probiotics with prebiotics on alginate matrix and its effect on viability in simulated gastric environment. *LWT—Food Science and Technology,* 57(1), Article 419-425.

[25] Zaeim, D., Jamab, M. S., Ghorani, B., Kadkhodaee, R., Liu, W., & Tromp, R. H. (2020). Microencapsulation of probiotics in multi-polysaccharide microcapsules by electro-hydrodynamic atomization and incorporation into ice-cream formulation. *Food Structure,* 25, Article 100147.

[26] Poletto, G., Raddatz, G. C., Cichoski, A. J., Zepka, L. Q., Lopes, E. J., Barin, J. S., Wagner, R., & de Menezes, C. R. (2019). Study of viability and storage stability of *Lactobacillus acidophillus* when encapsulated with the prebiotics rice bran, inulin and Hi-maize. *Food Hydrocolloids,* 95, Article 238-244.

[27] Qin, X. S., Luo, Z. G., & Li, X. L. (2020). An enhanced pH-sensitive carrier based on alginate-Ca-EDTA in a set-type W1/O/W2 double emulsion model stabilized with WPI-EGCG covalent conjugates for probiotics colon-targeted release. *Food Hydrocolloids,* 113, Article 106460.

[28] Kumherová, M., Veselá, K., Jokešová, K., Klojdová, I., & Horáčková, Š. (2020). Influence of co-encapsulation of *Bifidobacterium animalis* subsp. *lactis* Bb12 with inulin and ascorbic acid on its viability. *Czech Journal of Food Science,* 38(1), Article 57-62.

[29] Huebner, J., Wehling, R. L. & Hutkins, R. W. (2007). Functional activity of commercial prebiotics. *International Dairy Journal,* 17, Article 770-775.

The invention claimed is:

1. A method of preparing a bigel, comprising co-encapsulated probiotics cells and soluble prebiotic dietary fibers, the method comprising steps of:

a) extracting the soluble prebiotic dietary fibers from berry pomace;

b) preparing a suspension of probiotic cells;

c) obtaining a hydrogel phase by dissolving collagen and the extracted soluble dietary fiber obtained in step a) in distilled water and incubating;

d) obtaining an oleogel phase by dissolving a gelator in vegetable oil and incubating;

e) homogenizing the oleogel phase obtained in step d) and the hydrogel phase obtained in step c) in two stages by:

-first, mixing the oleogel phase and the hydrogel phase to obtain a homogenized mixture;

-second, cooling down the homogenized mixture until 55 °C, adding the suspension of probiotic cells from step b), and additionally homogenizing the mixture;

f) immediately after homogenization, transferring the mixture to an ice bath to induce gelation of both phases, and optionally, storing the obtained bigel in cold conditions.

2. The method of claim 1, wherein the step a) of extracting the soluble prebiotic dietary fiber from berry pomace is performed in the following substeps:

a1) fresh or defrosted berry pomace is dried to a moisture content of 7-9% by using a drying method selected from hot air drying at 35-40 °C for 48-72 hours or freeze-drying at −50 °C and 0.5 mbar for 24-48 hours to obtain dried pomace;

a2) before usage dry pomace is milled to 0.2-0.25 mm particles to obtain a dry pomace powder;

a3) the dry pomace powder is mixed with water in a ratio of 1:10, stirred for 10-15 min and centrifuged at 8000-10000 rev/sec for 15 min.;

a4) a separated water-soluble fraction obtained from the centrifugation of the dry pomace powder and water mixture is mixed with ethanol in a ratio of 5:95 and stirred for 5-10 min.;

a5) the mixture from the previous step is filtered to obtain a sediment;

a6) after filtering, the sediment is dried by using any of the following drying methods: hot air of 35-40 °C during 48-72 hours, freeze-drying in −50 °C, 0.5 mbar, during 24-48 hours; and wherein optionally after step a1) the dried pomace is cooled, weighed, and stored in sealed packages in a ventilated room with a relative humidity of no higher than 75% and an ambient temperature not exceeding 20 °C up to 4 months, or refrigerated at 4 °C up to 12 months before step a2).

3. The method of claim 1, wherein in the step b) obtained probiotic cell suspension has to contain no less than $1.3 \times 10^{11}$ cfu/ml of viable cells, for using it in the bigel preparation.

4. The method of claim 1, wherein the step b) of preparing the suspension of probiotic cells is performed in the following substeps:

Activating probiotic strains using MRS broth and incubating at 37 °C for 22 hours aerobically, wherein the MRS broth is for the enrichment, cultivation, and isolation of *Lactobacillus* species;

after incubation, extracting the probiotic cells by centrifugation at 6000 rpm for 10 min at +4 °C;

washing the extracted probiotic cells with sterile saline water;

wherein the obtained probiotic cell suspension has to contain no less than $1.3 \times 10^{11}$ cfu/ml of viable cells, for using it in the bigel preparation.

5. The method of claim 1, wherein the step c) of preparing the hydrogel phase is performed under the following conditions:

60 g of collagen per 100 g of the hydrogel phase and 1.34 g of soluble dietary fiber per 100 g of the hydrogel phase dissolved in distilled water and incubated at 85 °C for 30 min continuously mixing.

6. The method of claim 1, wherein the step d) preparing the oleogel phase is performed under the following conditions:

9 g of carnauba wax as a gelator per 100 g of the oleogel phase dissolved in vegetable oil and incubated at 85 °C for 30 min.

7. The method of claim 1, wherein the step e) of homogenizing the oil and water phases is performed under the following conditions:

mixing the oleogel and hydrogel phases at ratio 25:75, and homogenizing the mixture for 60 s at 15 000 rpm, while maintaining the temperature at 85 °C;

cooling down the homogenized mixture until 55 °C, adding a total of 1 ml/100 g of the suspension of probiotic cells, the suspension containing 1.3×10^11 cfu/ml of viable cells, and additionally homogenizing the mixture at 11000 rpm for 60 s.

8. The method of claim 1, wherein the step f) of gelating the homogenized mixture is performed under the following conditions:

transferring the mixture to the ice bath to induce gelation of both phases, and optionally, the obtained bigel is stored at +4 °C or −18 °C.

* * * * *